(12) United States Patent
Morita

(10) Patent No.: US 12,354,189 B2
(45) Date of Patent: Jul. 8, 2025

(54) INFORMATION PROCESSING DEVICE, INFORMATION PROCESSING METHOD, PROGRAM, AND RADIOGRAPHY SYSTEM

(71) Applicant: FUJIFILM CORPORATION, Tokyo (JP)

(72) Inventor: Junya Morita, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 307 days.

(21) Appl. No.: 17/666,589

(22) Filed: Feb. 8, 2022

(65) Prior Publication Data
US 2022/0270306 A1 Aug. 25, 2022

(30) Foreign Application Priority Data
Feb. 19, 2021 (JP) .................................. 2021-025617

(51) Int. Cl.
*G06T 11/00* (2006.01)
*A61B 6/02* (2006.01)
(Continued)

(52) U.S. Cl.
CPC ............ *G06T 11/005* (2013.01); *A61B 6/025* (2013.01); *A61B 6/463* (2013.01); *A61B 6/502* (2013.01);
(Continued)

(58) Field of Classification Search
None
See application file for complete search history.

(56) References Cited

U.S. PATENT DOCUMENTS

| 6,081,577 A * | 6/2000 | Webber ................. A61B 6/548 378/98.12 |
| 7,760,924 B2 * | 7/2010 | Ruth ....................... G06T 15/08 382/128 |

(Continued)

FOREIGN PATENT DOCUMENTS

| JP | 2009-240435 A | 10/2009 |
| JP | 2010-51455 A | 3/2010 |

(Continued)

OTHER PUBLICATIONS

English language translation of the following: Office action dated May 28, 2024 from the JPO in a Japanese patent application No. 2021-025617 corresponding to the instant patent application. This office action translation is submitted now in order to supplement the understanding of the cited references which are being disclosed in the instant Information Disclosure Statement.

*Primary Examiner* — Vikkram Bali
(74) *Attorney, Agent, or Firm* — SOLARIS Intellectual Property Group, PLLC

(57) ABSTRACT

The information processing device includes a processor. The processor performs: a reconstruction process of reconstructing a plurality of tomographic images from a plurality of projection images obtained by tomosynthesis imaging that irradiates an object with radiation from a radiation source at a plurality of radiation source positions; a synthesis process of synthesizing the plurality of tomographic images to generate a synthesized two-dimensional image as a projection image based on a virtual radiation source position; an anatomical structure extraction process of extracting anatomical structures from a projection image corresponding to a radiation source position closest to the virtual radiation source position among the plurality of radiation source positions; and a display process of displaying an extraction (Continued)

result of the anatomical structures on a display device together with the synthesized two-dimensional image.

14 Claims, 21 Drawing Sheets

(51) Int. Cl.
*A61B 6/46* (2024.01)
*A61B 6/50* (2024.01)
*G06T 7/00* (2017.01)
*G06T 7/70* (2017.01)

(52) U.S. Cl.
CPC .............. *G06T 7/0012* (2013.01); *G06T 7/70* (2017.01); *G06T 2207/10112* (2013.01); *G06T 2207/30068* (2013.01)

(56) References Cited

U.S. PATENT DOCUMENTS

| | | |
|---|---|---|
| 2009/0123052 A1 | 5/2009 | Ruth et al. |
| 2010/0054557 A1* | 3/2010 | Morita ................. A61B 6/5217 382/128 |
| 2019/0096098 A1* | 3/2019 | Fukuda ................. G06T 11/006 |

FOREIGN PATENT DOCUMENTS

| | | |
|---|---|---|
| JP | 2010-051456 A | 3/2010 |
| JP | 2012-512669 A | 6/2012 |
| JP | 2014-128716 A | 7/2014 |
| WO | 2010/059920 A2 | 5/2010 |

\* cited by examiner

RADIATION SOURCE POSITION CLOSEST TO PK

FIG. 12

| EVALUATION ITEM | PERFECT SCORE | EVALUATION POINT | DEDUCTION POINT |
|---|---|---|---|
| LEFT-RIGHT SYMMETRY OF BREAST | 10 | 7.5 | -2.5 |
| LATERALITY OF NIPPLE | 10 | 6.0 | -4.0 |
| PECTORALIS MAJOR MUSCLE | 10 | 9.0 | -1.0 |
| RETROMAMMARY SPACE | 10 | 9.0 | -1.0 |
| INFRAMAMMARY REGION | 10 | 8.5 | -1.5 |
| EXTENSIBILITY OF MAMMARY GLAND | 10 | 7.5 | -2.5 |
| TOTAL EVALUATION VALUE S | | | -12.5 |

FIG. 13

| EVALUATION RANK | TOTAL EVALUATION VALUE S |
|---|---|
| A | $0 \geq S > -5.4$ |
| B | $-5.4 \geq S > -10.8$ |
| C | $-10.8 \geq S > -18.0$ |
| D | $-18.0 \geq S > -36.0$ |
| E | $-36.0 \geq S$ |

POSITIONING EVALUATION

EVALUATION VALUE S = | 0.5 − Xc/(Xmax + Xmin) |

INFORMATION PROCESSING DEVICE, INFORMATION PROCESSING METHOD, PROGRAM, AND RADIOGRAPHY SYSTEM

CROSS-REFERENCE TO RELATED APPLICATIONS

The present application claims priority under 35 U.S.C. § 119 to Japanese Patent Application No. 2021-025617 filed on Feb. 19, 2021. The above application is hereby expressly incorporated by reference, in its entirety, into the present application.

BACKGROUND

1. Technical Field

The technology of the present disclosure relates to an information processing device, an information processing method, a program, and a radiography system.

2. Description of the Related Art

In radiography, it is extremely important to properly position an object with respect to an imaging range (hereinafter, referred to as "positioning") and to perform imaging in order to generate a radiographic image suitable for diagnosis. For example, in a case in which the object is out of the imaging range due to improper positioning, it is difficult to make an appropriate diagnosis. Therefore, a radiographer needs to determine whether the positioning of the object is good or bad on the basis of the captured radiographic image and to determine whether or not reimaging is required on the basis of the determination result.

JP2010-051456A discloses a technique which analyzes a radiographic image to extract anatomical structures and which evaluates whether the positioning of an object is good or bad, in order to assist a radiographer in determining whether the positioning of the object is good or bad. The object is, for example, the breast of a subject.

In recent years, radiography apparatuses, such as mammography apparatuses, having a tomosynthesis imaging function have come into widespread use. The tomosynthesis imaging function can reconstruct a plurality of projection images obtained by irradiating the object with radiation from a radiation source at a plurality of radiation source positions to generate a three-dimensional image consisting of a plurality of tomographic images.

In addition, JP2014-128716A discloses a technique which synthesizes a plurality of tomographic images acquired by tomosynthesis imaging to generate a two-dimensional image (hereinafter, referred to as a synthesized two-dimensional image). In the related art, a two-dimensional image is acquired by normal radiography in addition to the tomosynthesis imaging. However, a synthesized two-dimensional image is generated from the tomographic images obtained by the tomosynthesis imaging, which makes it possible to reduce the exposure dose of the part to be diagnosed and to shorten the imaging time.

SUMMARY

In the radiography apparatus having the tomosynthesis imaging function, it is considered to evaluate whether the positioning of the object is good or bad using, for example, the synthesized two-dimensional image. Since the synthesized two-dimensional image is generated by a reconstruction process of generating tomographic images and a synthesis process of synthesizing a plurality of tomographic images, a positioning evaluation process based on the synthesized two-dimensional image depends on the reconstruction process and the synthesis process.

For the reconstruction process and the synthesis process, new methods are being researched and developed every day in order to improve the quality of the tomographic image and the synthesized two-dimensional image. Therefore, in a case in which either the reconstruction process or the synthesis process is changed to a new method, it is necessary to re-optimize the positioning evaluation process (for example, the anatomical structure extraction process). As described above, in a case in which positioning is evaluated using a synthesized two-dimensional image, it is necessary to re-optimize the process whenever either the reconstruction process or the synthesis process is changed, which is complicated. Therefore, there is a demand for a method that can evaluate whether the positioning of an object is good or bad without using a synthesized two-dimensional image.

An object of the technology of the present disclosure is to provide an information processing device, an information processing method, a program, and a radiography system that can evaluate whether the positioning of an object is good or bad without using a synthesized two-dimensional image.

In order to achieve the above object, according to the present disclosure, there is provided an information processing device comprising a processor. The processor performs: a reconstruction process of reconstructing a plurality of tomographic images from a plurality of projection images obtained by tomosynthesis imaging that irradiates an object with radiation from a radiation source at a plurality of radiation source positions; a synthesis process of synthesizing the plurality of tomographic images to generate a synthesized two-dimensional image as a projection image based on a virtual radiation source position; an anatomical structure extraction process of extracting anatomical structures from a projection image corresponding to a radiation source position closest to the virtual radiation source position among the plurality of radiation source positions; and a display process of displaying an extraction result of the anatomical structures on a display device together with the synthesized two-dimensional image.

Preferably, the processor starts the anatomical structure extraction process before or during the synthesis process.

Preferably, the processor performs a positioning evaluation process of evaluating at least one evaluation item on the basis of the extraction result of the anatomical structures to evaluate whether positioning of the object is good or bad.

Preferably, the processor displays a result of evaluating whether the positioning is good or bad by the positioning evaluation process on the display device together with the synthesized two-dimensional image in the display process.

Preferably, the projection image is a breast image obtained by imaging a breast as the object.

Preferably, the anatomical structures include at least one of the breast, a mammary gland, a pectoralis major muscle, or a nipple.

Preferably, the evaluation items include at least one of a left-right symmetry of the breast, a laterality of the nipple, the pectoralis major muscle, a retromammary space, an inframammary region, or an extensibility of the mammary gland.

Preferably, the processor performs a virtual radiation source position determination process of determining the virtual radiation source position before the synthesis process.

Preferably, in the virtual radiation source position determination process, the processor determines the virtual radiation source position on the basis of one projection image selected by analyzing the plurality of projection images.

Preferably, in the virtual radiation source position determination process, the processor determines the virtual radiation source position on the basis of one projection image selected by a user through an operation device among the plurality of projection images.

According to the present disclosure, there is provided an information processing method comprising: reconstructing a plurality of tomographic images from a plurality of projection images obtained by tomosynthesis imaging that irradiates an object with radiation from a radiation source at a plurality of radiation source positions; synthesizing the plurality of tomographic images to generate a synthesized two-dimensional image as a projection image based on a virtual radiation source position; extracting anatomical structures from a projection image corresponding to a radiation source position closest to the virtual radiation source position among the plurality of radiation source positions; and displaying an extraction result of the anatomical structures on a display device together with the synthesized two-dimensional image.

According to the present disclosure, there is provided a program that causes a computer to perform: a reconstruction process of reconstructing a plurality of tomographic images from a plurality of projection images obtained by tomosynthesis imaging that irradiates an object with radiation from a radiation source at a plurality of radiation source positions; a synthesis process of synthesizing the plurality of tomographic images to generate a synthesized two-dimensional image as a projection image based on a virtual radiation source position; an anatomical structure extraction process of extracting anatomical structures from a projection image corresponding to a radiation source position closest to the virtual radiation source position among the plurality of radiation source positions; and a display process of displaying an extraction result of the anatomical structures on a display device together with the synthesized two-dimensional image.

According to the present disclosure, there is provided a radiography system comprising: a radiography apparatus; and an information processing device. The radiography apparatus generates a plurality of projection images obtained by tomosynthesis imaging that irradiates an object with radiation from a radiation source at a plurality of radiation source positions. The information processing device performs a reconstruction process of reconstructing a plurality of tomographic images from the plurality of projection images, a synthesis process of synthesizing the plurality of tomographic images to generate a synthesized two-dimensional image as a projection image based on a virtual radiation source position, an anatomical structure extraction process of extracting anatomical structures from a projection image corresponding to a radiation source position closest to the virtual radiation source position among the plurality of radiation source positions, and a display process of displaying an extraction result of the anatomical structures on a display device together with the synthesized two-dimensional image.

According to the technology of the present disclosure, it is possible to provide an information processing device, an information processing method, a program, and a radiography system that can evaluate whether the positioning of an object is good or bad without using a synthesized two-dimensional image.

BRIEF DESCRIPTION OF THE DRAWINGS

Exemplary embodiments according to the technique of the present disclosure will be described in detail based on the following figures, wherein:

FIG. 12 is a diagram illustrating an example of evaluation points for each evaluation item, FIG. 13 is a diagram illustrating an example of a classification table for calculating an evaluation rank.

DETAILED DESCRIPTION

Hereinafter, embodiments according to the technology of the present disclosure will be described with reference to the drawings.

Figure 1:
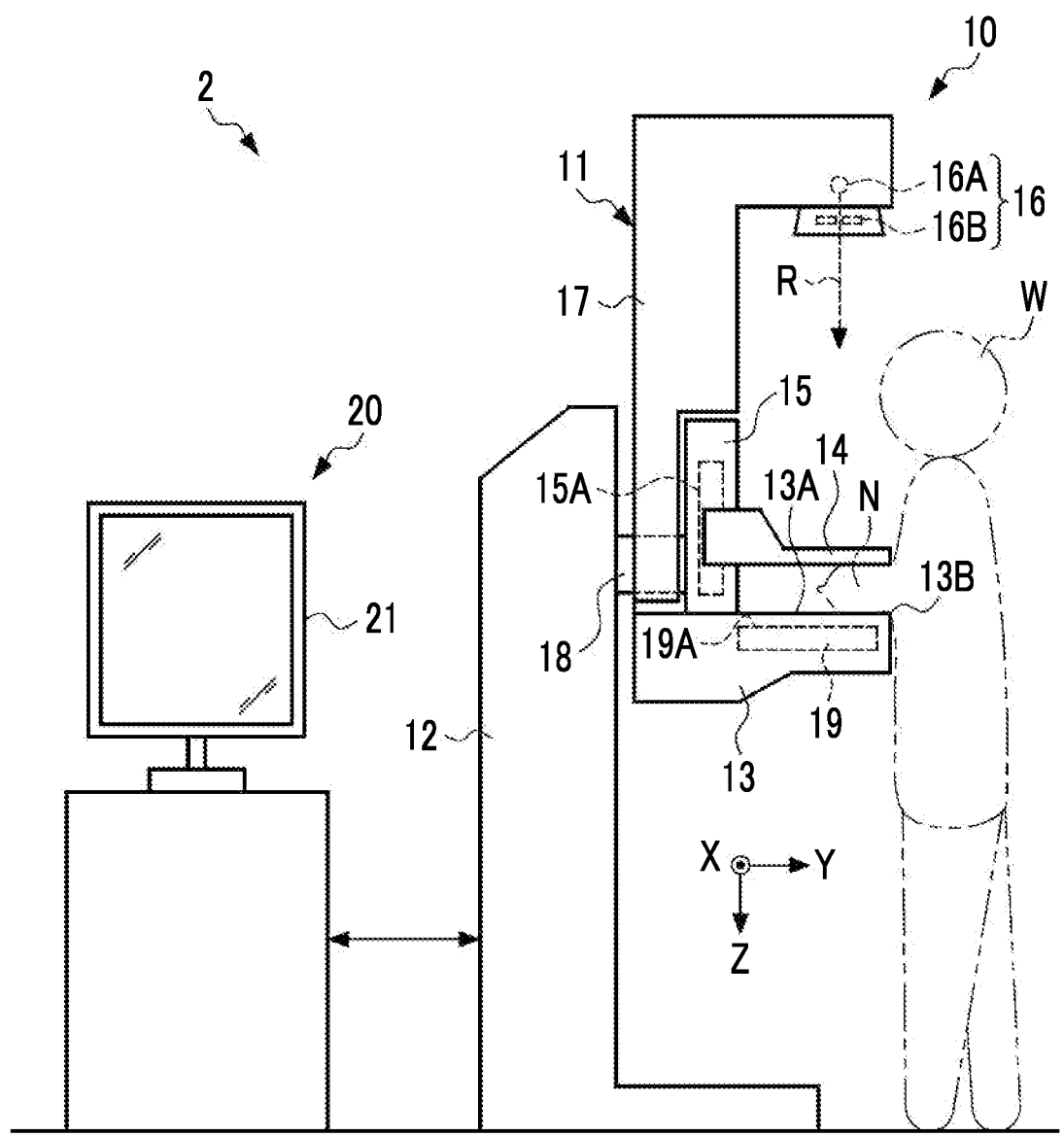
FIG. 1 is a schematic diagram illustrating a configuration of a radiography system.

First, the configuration of a radiography system according to an embodiment will be described. FIG. 1 illustrates the configuration of a radiography system 2 according to this embodiment.

As illustrated in FIG. 1, the radiography system 2 is operated by a radiographer, such as a doctor or a radiology technician, and has a function of capturing a radiographic image on the basis of information (for example, an imaging menu) input from an external system (for example, a radiology information system (RIS)) through a console 20.

The radiography system 2 includes a mammography apparatus 10 and the console 20. The mammography apparatus 10 is an example of a "radiography apparatus" according to the technology of the present disclosure. The console 20 is an example of an "information processing device" according to the technology of the present disclosure.

The mammography apparatus 10 is a radiography apparatus that performs radiography on a breast N of a subject W as an object to be imaged. In addition, the mammography apparatus 10 may be an apparatus that images the breast N of the subject W not only in a state in which the subject W is standing but also in a sitting state in which the subject W is sitting on a chair or the like, or may be a radiography apparatus that can at least separately image the left and right breasts N of the subject W.

The mammography apparatus 10 has a measurement portion 11 that is provided on a front side of the apparatus and that has a substantially C-shape in a side view and a base portion 12 that supports the measurement portion 11 from a rear side of the apparatus.

The measurement portion 11 includes an imaging table 13 having a flat imaging surface 13A that comes into contact with the breast N of the subject W, a compression plate 14 for compressing the breast N against the imaging surface 13A of the imaging table 13, and a holding portion 15 that supports the imaging table 13 and the compression plate 14.

The compression plate 14 is formed of a member that transmits radiation. The compression plate 14 is formed of, for example, a thermoplastic material (for example, polyethylene terephthalate) which is a resin material. The compression plate 14 may be a compression plate having a concave shape in a cross-sectional view in which a bottom portion that comes into contact with the breast is surrounded by a wall portion. In addition, the compression plate 14 is referred to as a "compression plate" for convenience in the present disclosure. However, the compression plate 14 is not limited to the compression plate using a plate-shaped member and may be, for example, a compression plate using a film-shaped member.

Further, the measurement portion 11 has a radiation source 16 that emits radiation R to the imaging surface 13A and a support portion 17 that is separated from the holding portion 15 and that supports the radiation source 16. The radiation source 16 is configured to include a radiation tube 16A that emits the radiation R and a collimator 16B that limits the irradiation field of the radiation R. The radiation source 16 irradiates the breast compressed by the compression plate 14 with the radiation R. The radiation R is, for example, an X-ray. In addition, the radiation R is represented by a straight line in FIG. 1. However, the radiation R emitted from the radiation source 16 has a conical shape.

Further, the measurement portion 11 is provided with a rotating shaft 18 that is rotatably supported by the base portion 12. The rotating shaft 18 is fixed to the support portion 17. Therefore, the rotating shaft 18 and the support portion 17 are rotated integrally.

The rotating shaft 18 is configured to be switchable between a state in which the rotating shaft 18 is rotated integrally with the holding portion 15 and a state in which the rotating shaft 18 is separated and idles. Specifically, each of the rotating shaft 18 and the holding portion 15 is provided with gears (not illustrated), and the gears are switchable between an engaged state and a non-engaged state. The rotating shaft 18 is driven by a motor (not illustrated). The rotating shaft 18 and the motor constitute a rotation mechanism 18A (see FIG. 4) for rotating the radiation source 16.

Further, the holding portion 15 supports the imaging table 13 such that the imaging surface 13A is separated from the radiation source 16 by a predetermined distance. Furthermore, the holding portion 15 holds the compression plate 14 such that a gap between the compression plate 14 and the imaging surface 13A is variable. Specifically, a movement mechanism 15A that moves the compression plate 14 is provided in the holding portion 15. The movement mechanism 15A is, for example, a linear actuator that includes a ball screw and a motor. The compression plate 14 is connected to the ball screw. The compression plate 14 is slid in a vertical direction (Z-axis direction) by the driving of the motor.

A radiation detector 19 is provided in the imaging table 13. The radiation detector 19 is disposed such that a detection surface 19A for detecting the radiation R is parallel to the imaging surface 13A. In FIG. 1, the imaging surface 13A is a flat surface including an X-axis direction and a Y-axis direction orthogonal to the Z-axis direction.

The radiation detector 19 detects the radiation R which has been emitted from the radiation source 16 and transmitted through the compression plate 14 and the breast N. The radiation detector 19 is a so-called flat panel detector. The radiation detector 19 has radiation detection pixels which are two-dimensionally arranged and detects the dose of the radiation R incident on each radiation detection pixel to generate a radiographic image.

The radiation detector 19 is, for example, an indirect-conversion-type radiation detector that converts the radiation R into visible light and converts the converted visible light into charge. In addition, the radiation detector 19 may be a direct-conversion-type radiation detector that directly converts the radiation R into charge.

The mammography apparatus 10 can perform tomosynthesis imaging in which the support portion 17 holding the radiation source 16 is rotated to irradiate the breast N as the object with the radiation R emitted from the radiation source 16 at a plurality of radiation source positions. The radiation detector 19 detects the radiation R transmitted through the breast N to generate a radiographic image whenever the radiation source 16 emits the radiation at each of the plurality of radiation source positions.

In this embodiment, the radiographic image generated by the radiation detector 19 of the mammography apparatus 10 is transmitted to the console 20. The console 20 has a control function of controlling the operation of the mammography apparatus 10. The console 20 controls the mammography apparatus 10 using the imaging menu or various kinds of information acquired from an external system or the like through a wireless communication local area network (LAN) or the like.

The console 20 is configured by a computer. The console 20 has a display unit 21 that displays various kinds of information. The display unit 21 is a display device such as a liquid crystal display or an organic electro luminescence (EL) display.

Figure 2:
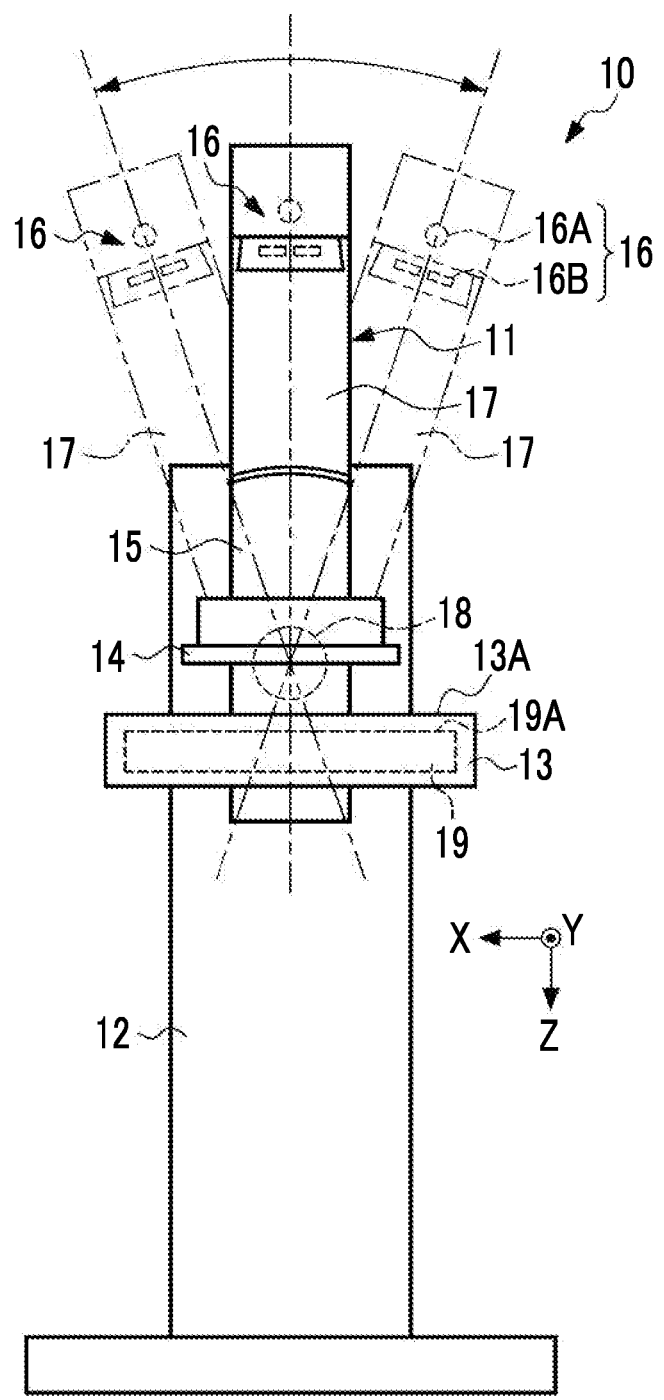
FIG. 2 is a front view of a mammography apparatus illustrating an operation of tomosynthesis imaging.

FIG. 2 illustrates the operation of the mammography apparatus 10 in the tomosynthesis imaging. As illustrated in FIG. 2, in the tomosynthesis imaging, radiography is performed while the support portion 17 holding the radiation source 16 is rotated on the rotating shaft 18. In this case, the imaging table 13 and the compression plate 14 are fixed, and the radiation source 16 is moved in an arc shape by the rotation of the support portion 17.

Figure 3:
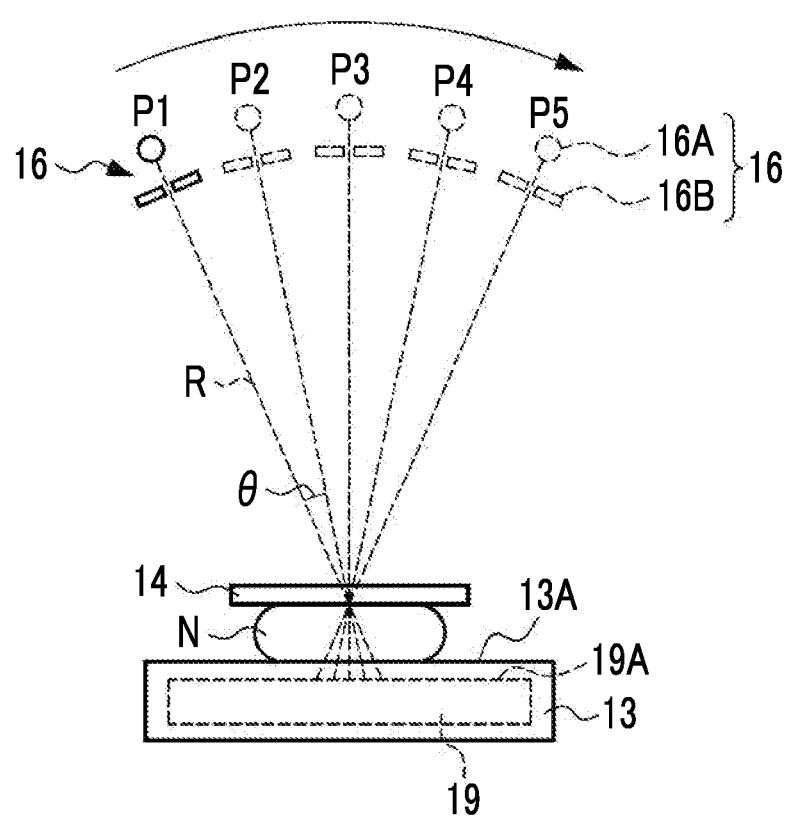
FIG. 3 is a diagram illustrating an example of a plurality of radiation source positions where radiation is emitted in the tomosynthesis imaging.

FIG. 3 illustrates an example of the plurality of radiation source positions where the radiation is emitted in the tomosynthesis imaging. P1 to P5 illustrated in FIG. 3 indicate the radiation source positions where the radiation source 16 emits the radiation R. The position of the radiation source 16 is changed in order from the radiation source position P1 which is an initial position to the radiation source position P5 which is a final position. The radiation source position is changed by a predetermined angle θ. Assuming that the change range of the radiation source position is ±20 degrees, the angle θ is 10 degrees.

In addition, the number of radiation source positions is five in FIG. 3. However, the number of radiation source positions is not limited thereto. That is, in the tomosynthesis imaging, radiography may be performed at n radiation source positions P1 to Pn.

In general, in a case in which the tomosynthesis imaging is performed, the breast N of the subject W is irradiated with the radiation n times. Therefore, the dose of the radiation R corresponding to one irradiation operation is reduced such that a radiation exposure dose does not increase. For example, the dose corresponding to one irradiation operation is set such that the total dose of the radiation corresponding to n irradiation operations is the same as that in normal two-dimensional imaging. The two-dimensional imaging is normal radiography in which the radiation source 16 is fixed at one radiation source position and the breast N is irradiated with radiation to generate one projection image.

In addition, the mammography apparatus 10 according to this embodiment can perform cranio & caudal (CC) imaging and mediolateral-oblique (MLO) imaging on the breast N.

In the CC imaging, the posture of the holding portion 15 is adjusted to a state in which the imaging surface 13A faces upward, and the posture of the support portion 17 is adjusted to a state in which the radiation source 16 is located on an upper side of the imaging surface 13A. Therefore, the CC imaging is performed by irradiating the breast N with the radiation R from the radiation source 16 in a direction from a head to a foot of the subject W in a standing state.

Further, in the MLO imaging, the posture of the holding portion 15 is adjusted such that the imaging table 13 is rotated at an angle that is equal to or greater than 45° and less than 90° with respect to that in the CC imaging. Furthermore, in the MLO imaging, the breast N is positioned such that an axilla of the subject W comes into contact with a side wall corner portion 13B (see FIG. 1) of the imaging table 13 which is located on the front side of the apparatus. Therefore, the MLO imaging is performed by irradiating the breast N with the radiation R from the radiation source 16 in a direction from the center of the axis of the body of the subject W to the outside.

It is extremely important to properly position the breast N, which is the object, in an imaging range and to image the breast N in order to generate a radiographic image suitable for diagnosis. For example, in a case in which the breast N is out of the imaging range due to improper positioning, it is difficult to make an appropriate diagnosis.

Further, in the image diagnosis of breast cancer by mammography, a difference in X-ray absorption between a lesion and a normal tissue is very small, and the diagnosis of a minute lesion is required. Therefore, a high-quality image is required. Among factors that affect the quality of images, particularly, the imaging technique of the radiographer has a large influence on the quality of images. In a case in which positioning is improper, the improper positioning may be a factor that causes lesions to be missed.

On the other hand, it is very difficult for the radiographer, such as a radiology technician, to properly position the breast, and an advanced imaging technique is required, for example, for the following reasons: the size, shape, mammary gland density, and the like of the breast vary depending on the subject; and mammography is a special imaging method that compresses the breast in order to fully expand the mammary gland. Therefore, the console 20 according to this embodiment has a function of evaluating whether positioning is good or bad on the basis of the image of the breast obtained by radiography.

Figure 4:
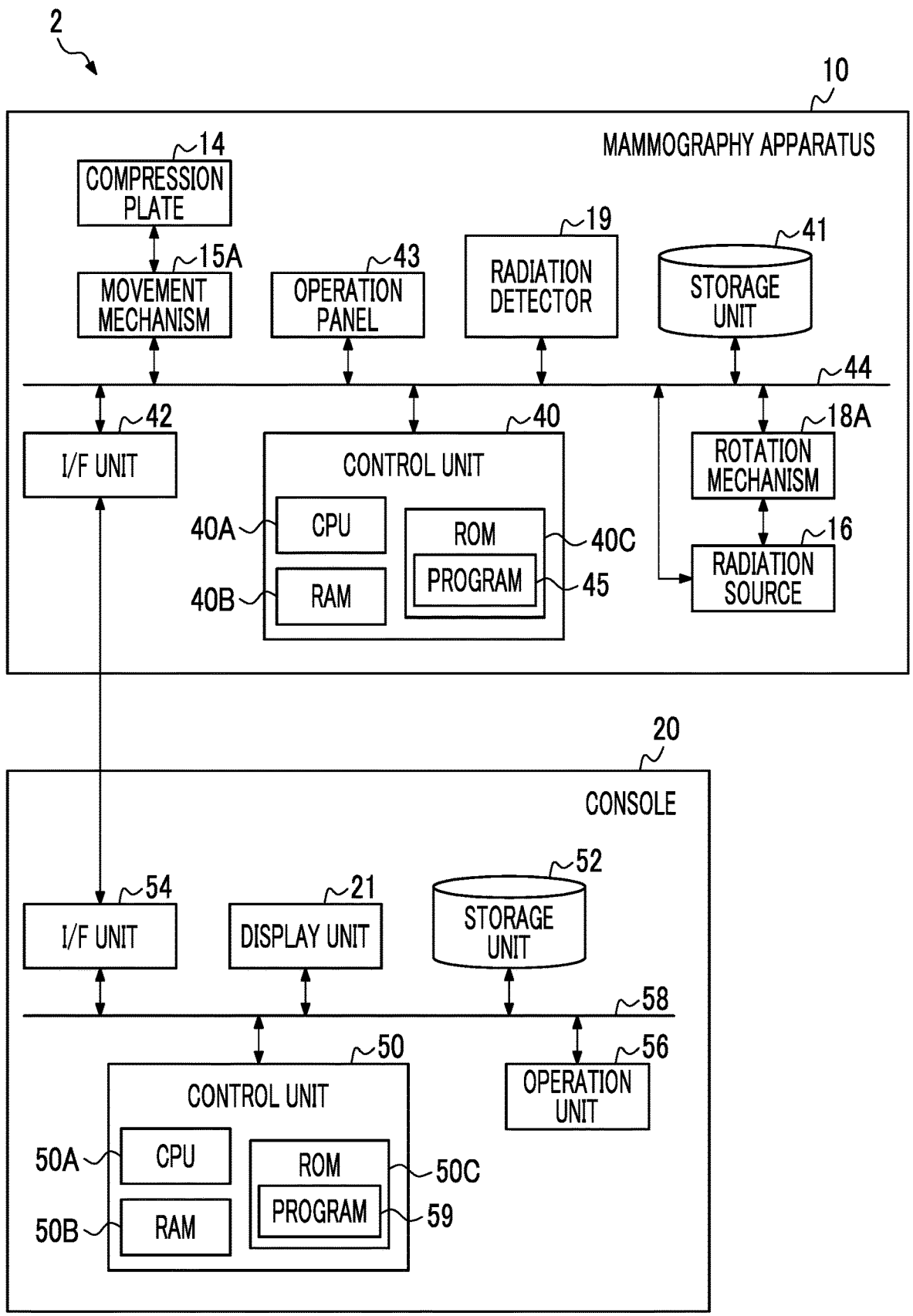
FIG. 4 is a block diagram illustrating an example of a hardware configuration of the radiography system.

FIG. 4 illustrates an example of the hardware configuration of the radiography system 2. The mammography apparatus 10 comprises the radiation source 16, the rotation mechanism 18A, the compression plate 14, the movement mechanism 15A, the radiation detector 19, a control unit 40, a storage unit 41, an interface (I/F) unit 42, and an operation panel 43. The radiation source 16, the rotation mechanism 18A, the movement mechanism 15A, the radiation detector 19, the control unit 40, the storage unit 41, the I/F unit 42, and the operation panel 43 are connected to each other through a bus 44 such that they can transmit and receive various kinds of information.

The control unit 40 includes a central processing unit (CPU) 40A, a random access memory (RAM) 40B, and a read only memory (ROM) 40C. Various kinds of data including a program 45 executed by the CPU 40A are stored in the ROM 40C in advance. The RAM 40C has a function of temporarily storing various kinds of data.

The storage unit 41 is composed of, for example, a hard disk drive (HDD) or a solid state drive (SSD). The storage unit 41 stores the radiographic image generated by the radiation detector 19.

The I/F unit 42 has a function of transmitting and receiving various kinds of information to and from the console 20 using wireless communication or wired communication.

The operation panel 43 is composed of, for example, a touch panel display, receives information input by the user, and displays the information. For example, the user can check imaging conditions and input instructions related to imaging through the operation panel 43. The control unit 40 controls various operations of the mammography apparatus 10 on the basis of the instructions input via the operation panel 43.

The movement mechanism 15A moves the compression plate 14 on the basis of an instruction from the control unit 40. Further, the rotation mechanism 18A rotates the radiation source 16 on the basis of an instruction from the control unit 40.

The console 20 comprises a control unit 50, a storage unit 52, an I/F unit 54, a display unit 21, and an operation unit 56. The control unit 50, the storage unit 52, the I/F unit 54, the display unit 21, and the operation unit 56 are connected to each other through a bus 58 such that they can transmit and receive various kinds of information.

The control unit 50 includes, for example, a CPU 50A, a RAM 50B, and a ROM 50C. Various kinds of data including a program 59 executed by the CPU 50A are stored in the ROM 50C in advance. The RAM 50B has a function of temporarily storing various kinds of data.

The I/F unit 54 has a function of transmitting and receiving various kinds of information to and from the mammography apparatus 10 and an external device (not illustrated) using wireless communication or wired communication. The external device is, for example, a radiology information system (RIS).

The operation unit 56 is composed of, for example, a keyboard, a mouse, a touch panel, and a touch pen. The operation unit 56 is used by the user to input, for example, instructions related to the capture of a radiographic image or various kinds of information. In addition, in a case in which the operation unit 56 is a touch panel, the operation unit 56 can be integrated with the display unit 21. The operation unit 56 corresponds to an "operation device" according to the technology of the present disclosure.

Figure 5:
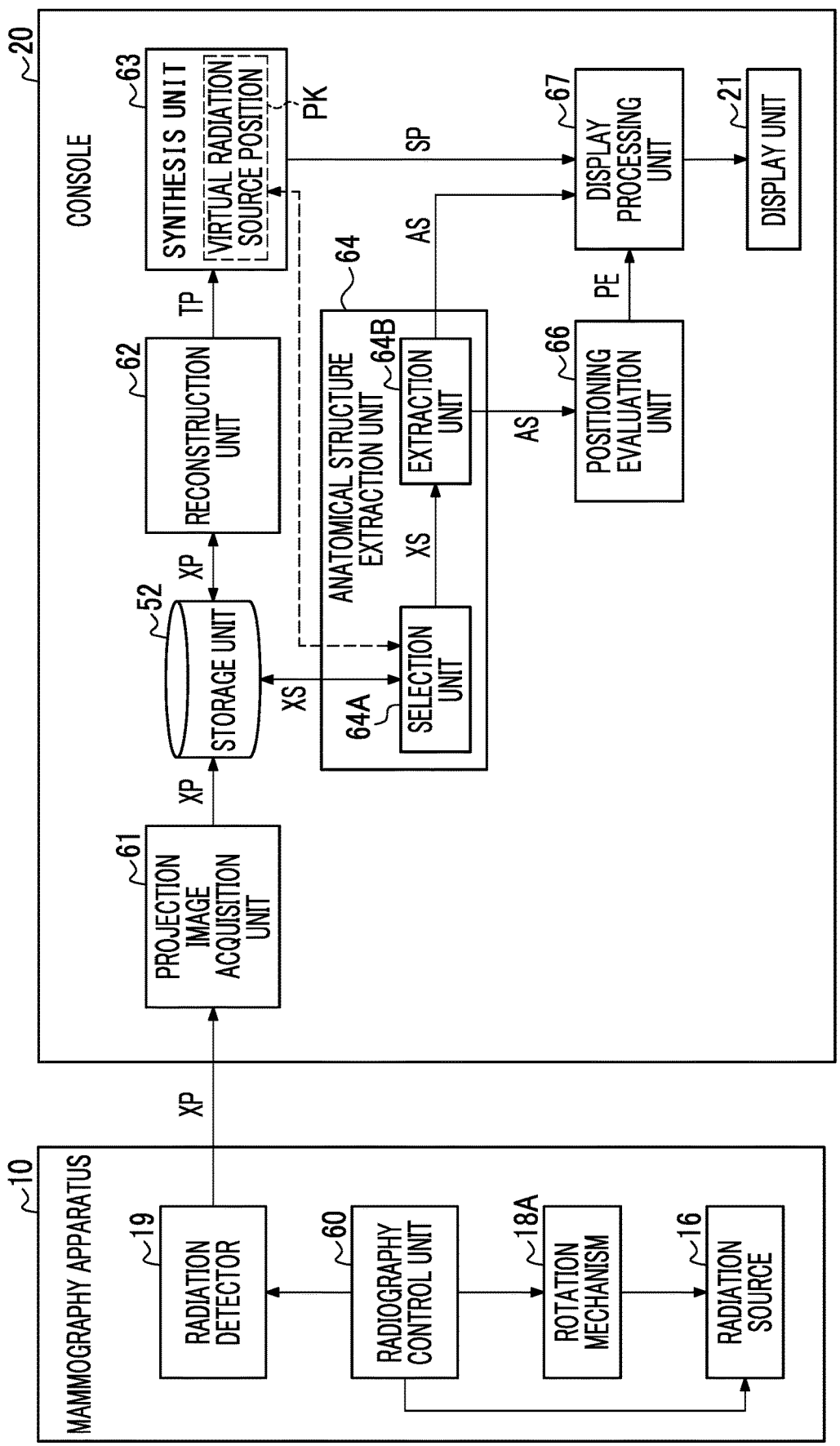
FIG. 5 is a block diagram illustrating an example of a functional configuration of the mammography apparatus and a console.

FIG. 5 illustrates an example of the functional configuration of the mammography apparatus 10 and the console 20. As illustrated in FIG. 5, in the mammography apparatus 10, the control unit 40 (see FIG. 4) functions as a radiography control unit 60 that controls the rotation mechanism 18A, the radiation source 16, and the radiation detector 19 such that the tomosynthesis imaging is performed.

The radiography control unit 60 controls the rotation mechanism 18A such that the radiation source 16 is moved to emit the radiation R at each of the radiation source positions P1 to P5. Further, the radiography control unit 60 directs the radiation detector 19 to perform a radiation detection operation whenever the radiation source 16 emits the radiation R at each radiation source position. Hereinafter, the radiographic image generated by the radiation detector 19 is referred to as a "projection image XP".

In the console 20, the control unit 40 (see FIG. 4) functions as a projection image acquisition unit 61, a reconstruction unit 62, a synthesis unit 63, an anatomical structure extraction unit 64, a positioning evaluation unit 66, and a display processing unit 67. In this embodiment, the anatomical structure extraction unit 64 includes a selection unit 64A and an extraction unit 64B.

The projection image acquisition unit 61 performs a projection image acquisition process of acquiring a plurality of projection images XP obtained by the tomosynthesis imaging performed by the mammography apparatus 10 from the mammography apparatus 10. The projection image acquisition unit 61 stores the acquired plurality of projection images XP in the storage unit 52. In addition, imaging conditions including radiation source position information indicating at which radiation source position the image is obtained by radiography are added to the projection image XP.

The reconstruction unit 62 performs a reconstruction process of reconstructing a plurality of tomographic images TP from the plurality of projection images XP stored in the storage unit 52. The reconstruction unit 62 performs the reconstruction process using a known reconstruction method such as a back projection method or a shift addition method.

Figure 6:
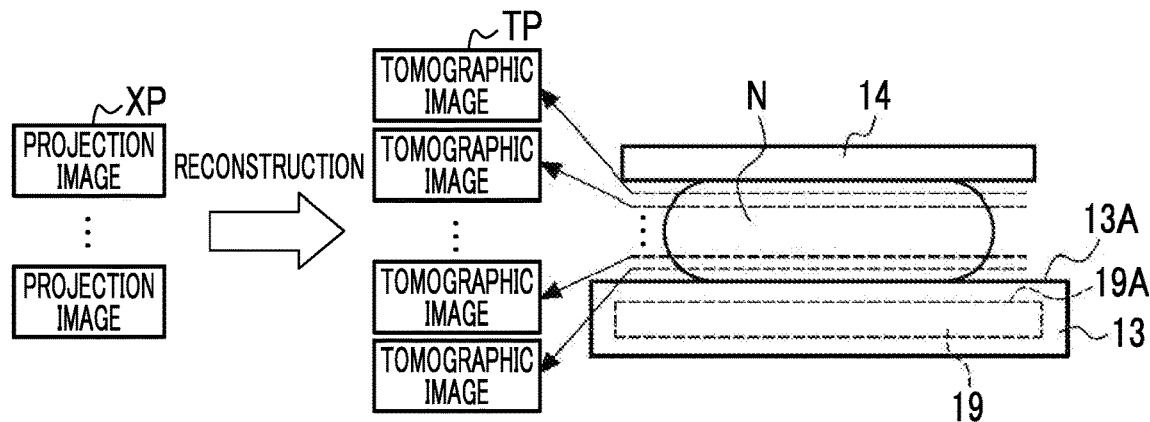
FIG. 6 is a diagram schematically illustrating a reconstruction process.

FIG. 6 schematically illustrates the reconstruction process. In FIG. 6, a tomographic plane is represented by a dashed straight line between the imaging table 13 and the compression plate 14. In this embodiment, the tomographic plane is a virtual plane that is parallel to the detection surface 19A of the radiation detector 19. The reconstruction unit 62 performs the reconstruction process on the basis of the plurality of projection images XP to generate the tomographic images TP indicating the images in the tomographic planes of the breast N. A distance between the tomographic planes is, for example, 1 mm.

The synthesis unit 63 performs a synthesis process on the basis of the plurality of tomographic images TP generated by the reconstruction unit 62 to generate a synthesized two-dimensional image SP. Specifically, the synthesis unit 63 performs a projection process on the plurality of tomographic images TP along a predetermined direction to generate the synthesized two-dimensional image. In addition, the synthesis unit 63 may generate the synthesized two-dimensional image SP using a minimum intensity projection method. Further, the synthesis unit 63 may perform an addition process of adding the corresponding pixel values along a predetermined direction to generate the synthesized two-dimensional image SP.

Figure 7:
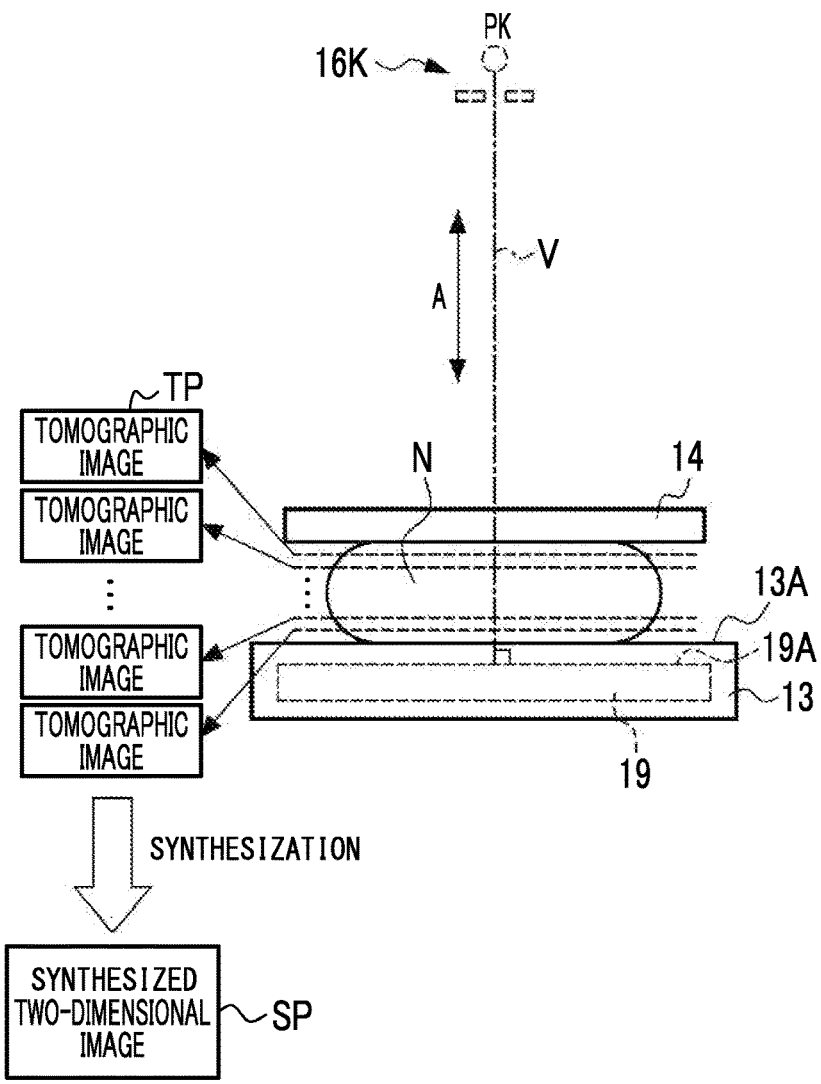
FIG. 7 is a diagram schematically illustrating a synthesis process.

FIG. 7 schematically illustrates the synthesis process. FIG. 7 illustrates an example in which the synthesis unit 63 performs the projection process along a direction A (that is, a direction orthogonal to the tomographic plane) orthogonal to the detection surface 19A of the radiation detector 19. In this case, the synthesized two-dimensional image SP generated by the synthesis unit 63 corresponds to a projection image in a case in which the breast N is irradiated with radiation from a virtual radiation source 16K which is located on a normal line V at the center of the detection surface 19A of the radiation detector 19. Hereinafter, the position of the virtual radiation source 16K is referred to as a virtual radiation source position PK. Therefore, the synthesis unit 63 is a processing unit that synthesizes a plurality of tomographic images TP to generate the synthesized two-dimensional image SP as the projection image based on the virtual radiation source position PK.

In this embodiment, the synthesis unit 63 holds the virtual radiation source position PK as setting information in advance. The virtual radiation source position PK may be changed by a setting operation using the operation unit 56. For example, the user can input an imaging angle using the operation unit 56. The synthesis unit 63 holds the virtual radiation source position PK corresponding to the imaging angle input through the operation unit 56 as the setting information. Here, the imaging angle is the incident angle of radiation on the detection surface 19A of the radiation detector 19 from the virtual radiation source position PK.

In a case in which the virtual radiation source position PK can be changed as described above, the synthesis unit 63 changes the direction A in which the projection process or the addition process is performed on the plurality of tomographic images TP according to the virtual radiation source position PK. The virtual radiation source position PK is present in a direction along the direction A from the center of the rotating shaft 18 (see FIG. 2).

In this embodiment, the selection unit 64A acquires the setting information of the virtual radiation source position PK from the synthesis unit 63. The selection unit 64A performs a projection image selection process that specifies a radiation source position closest to the virtual radiation source position PK from the plurality of radiation source positions P1 to P5 (see FIG. 3) and selects the projection image XP corresponding to the specified radiation source position from the plurality of projection images XP stored in the storage unit 52.

Figure 8:
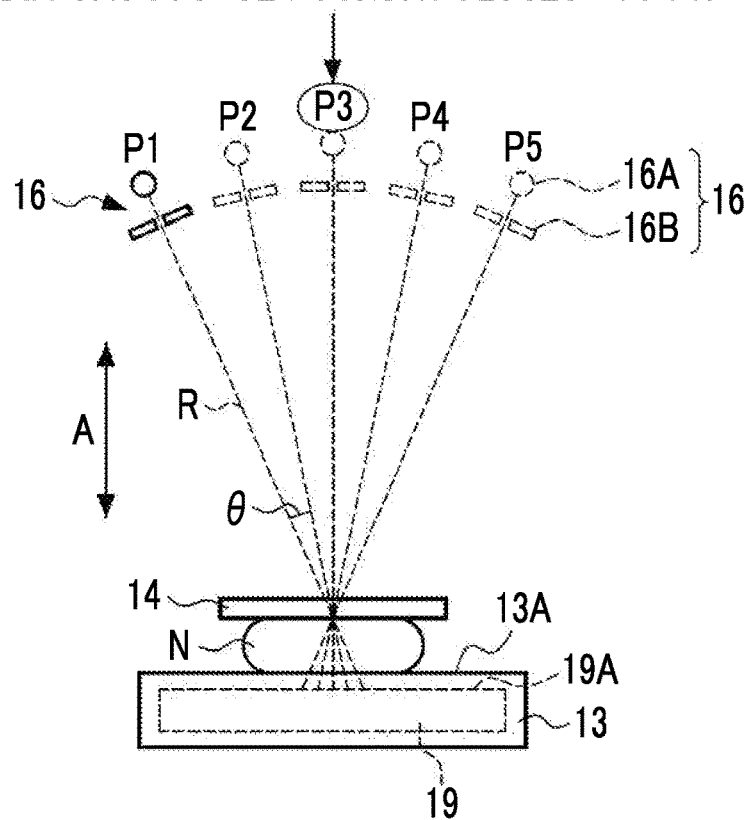
FIG. 8 is a diagram schematically illustrating a radiation source position process.

For example, as illustrated in FIG. 8, the selection unit 64A specifies the radiation source position closest to the virtual radiation source position PK from the plurality of radiation source positions P1 to P5. In the example illustrated in FIG. 8, the selection unit 64A specifies the radiation source position P3, which is an apex position, as the radiation source position closest to the virtual radiation source position PK. In addition, it goes without saying that the "radiation source position closest to the virtual radiation source position PK" includes the same position as the virtual radiation source position PK.

Figure 9:
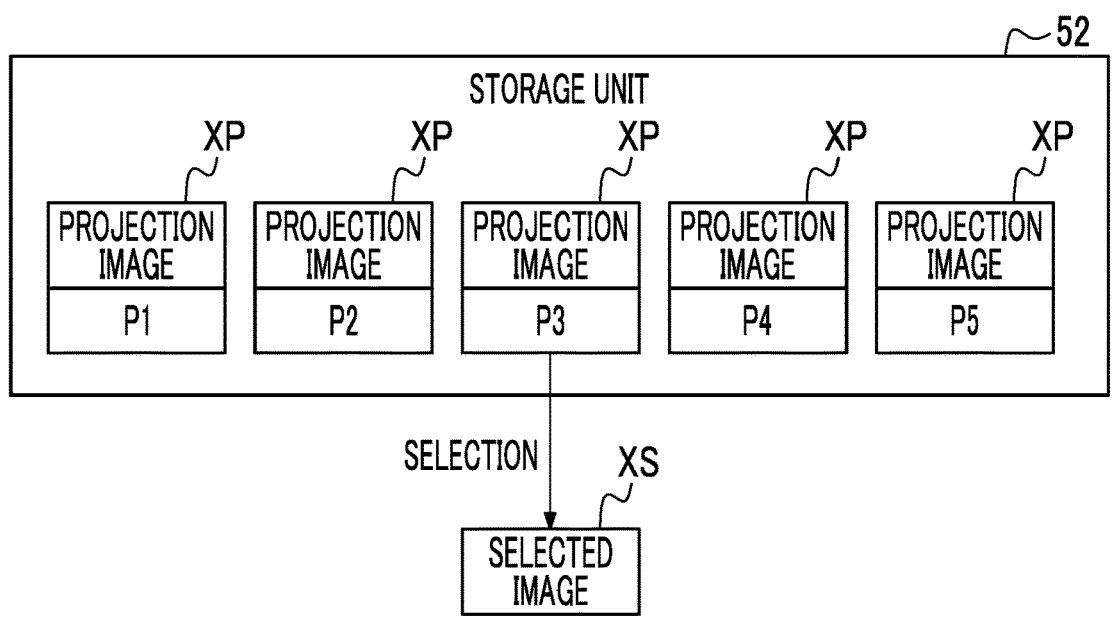
FIG. 9 is a diagram schematically illustrating a projection image selection process.

As illustrated in FIG. 9, the selection unit 64A selects the projection image XP corresponding to the specified radiation source position from the plurality of projection images XP stored in the storage unit 52. Hereinafter, the projection image XP selected by the selection unit 64A is referred to as a selected image XS. In this embodiment, the projection image XP corresponding to the radiation source position P3 is selected as the selected image XS.

The extraction unit 64B performs an anatomical structure extraction process of extracting anatomical structures on the basis of the selected image XS. The extraction unit 64B performs image analysis on the selected image XS to extract, for example, the breast, the mammary gland, the pectoralis major muscle, and the nipple as the anatomical structures. The anatomical structures extracted by the extraction unit 64B may include at least one of the breast, the mammary gland, the pectoralis major muscle, or the nipple.

Figure 10:
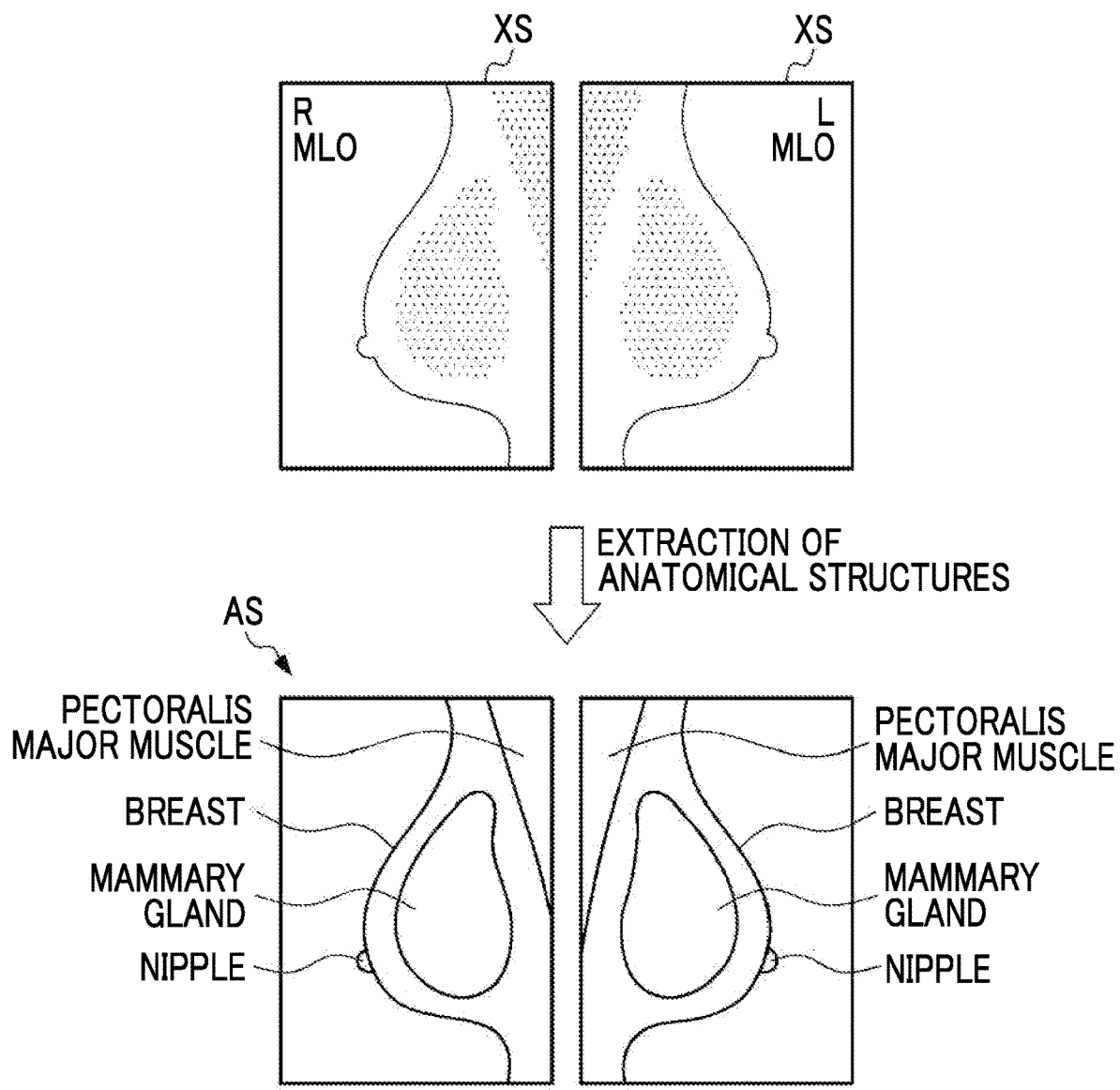
FIG. 10 is a diagram schematically illustrating an anatomical structure extraction process.

FIG. 10 schematically illustrates the anatomical structure extraction process. As illustrated in FIG. 10, in this embodiment, the extraction unit 64B extracts the anatomical structures from each of the selected image XS selected from a plurality of projection images XP obtained by performing the tomosynthesis imaging on the right breast N and the selected image XS selected from a plurality of projection images XP obtained by performing the tomosynthesis imaging on the left breast N. The selected image XS illustrated in FIG. 10 is an example of the breast image obtained by the MLO imaging. The selected image XS with "R" is the breast image of the right breast N. The selected image XS with "L" is the breast image of the left breast N.

Specifically, the extraction unit 64B extracts each structure according to the following procedure. A method for extracting the anatomical structures according to the following procedure is known, for example, in JP2010-051456A.

First, the extraction unit 64B divides the selected image XS into a breast region and a blank region. Since the blank region has a particularly high density on the image, a peak that appears on the high density side in a density histogram of the entire image corresponds to the blank region. A binarization process can be performed using, as a threshold value, a value obtained by subtracting a certain value from the peak value to divide the selected image into the breast region and the blank region.

Then, the extraction unit 64B extracts the contour (hereinafter, referred to as a skin line) of the breast region. Specifically, the extraction unit 64B sequentially searches for boundary points between the breast region and the blank region and connects the searched pixels to extract the skin line.

Then, the extraction unit 64B extracts a pectoralis major muscle region. Since the edge of the boundary between the pectoralis major muscle region and a fat region is relatively clear, the extraction unit 64B performs scanning using a differential operator from the skin line to the chest wall to extract a point with a large differential value as the boundary point of the pectoralis major muscle region. The extraction unit 64B calculates a curve that connects the extracted boundary points and extracts a region, which is on the chest wall side (a side opposite to the blank region) with respect to the curve, as the pectoralis major muscle region.

Then, the extraction unit 64B calculates a threshold value for extracting a mammary gland region from the density values of the pectoralis major muscle region and the fat region in the vicinity of the pectoralis major muscle region and extracts the mammary gland region on the basis of the calculated threshold value.

Then, the extraction unit 64B detects a nipple portion. The extraction unit 64B smooths the skin line to acquire a smoothed skin line and detects the nipple portion on the basis of the amount of separation between the acquired smoothed skin line and the skin line.

After extracting the anatomical structures, the extraction unit 64B outputs an extraction result AS of the anatomical structures to the display processing unit 67 and the positioning evaluation unit 66. The extraction result AS includes the characteristics (for example, the position, shape, and size) of the extracted anatomical structures.

In addition, the extraction unit 64B may analyze the selected image XS with a method using machine learning, such as deep learning, to extract the anatomical structures, instead of the method using image analysis.

The display processing unit 67 performs a display process of displaying the extraction result AS of the anatomical structures by the extraction unit 64B on the display unit 21 together with the synthesized two-dimensional image SP generated by the synthesis unit 63.

Figure 11:
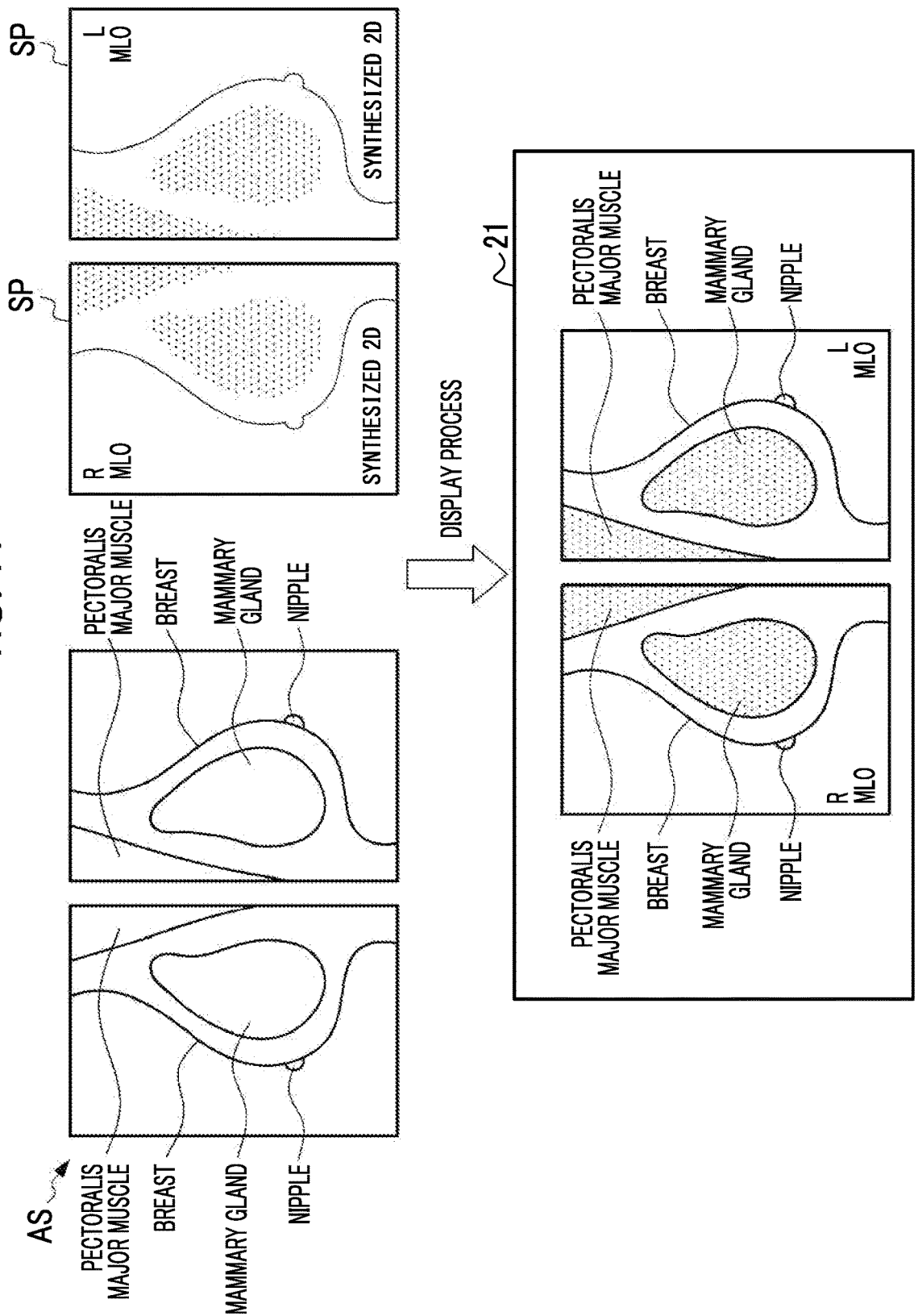
FIG. 11 is a diagram schematically illustrating a display process.

FIG. 11 schematically illustrates the display process. In this embodiment, the display processing unit 67 displays the extraction result AS of the anatomical structures on a pair of synthesized two-dimensional images SP indicating the left and right breasts N. In the example illustrated in FIG. 11, the extraction result AS is information indicating the contour of the anatomical structures and can specify the characteristics (the position, shape, and size) of each structure.

The extraction result AS of the anatomical structures is the extraction result obtained on the basis of the projection image XP (that is, the selected image XS) corresponding to the radiation source position P3 closest to the virtual radiation source position PK of the synthesized two-dimensional image SP. Therefore, the positional deviation between the structure included in the synthesized two-dimensional image SP and the contour of the structure displayed on the basis of the extraction result AS is minimized.

The radiographer can observe the extraction result AS of the anatomical structures displayed on the display unit 21 together with the synthesized two-dimensional image SP to evaluate whether the positioning of the left and right breasts N is good or bad with high accuracy.

In addition, one projection image XP includes a large amount of noise because the dose is low. On the other hand, the synthesized two-dimensional image SP is an image that has a small amount of noise and is suitable for diagnosis since it is generated from a plurality of projection images XP. Further, it is possible to perform a synthesis process suitable for diagnosis, such as a process of highlighting a structure in a specific tomographic plane, on the synthesized two-dimensional image SP. Therefore, it is preferable that the image used for analysis is the projection image XP which does not depend on the reconstruction process and the synthesis process. However, it is preferable that the image displayed on the display unit 21 is the synthesized two-dimensional image SP suitable for diagnosis.

The positioning evaluation unit 66 performs a positioning evaluation process of evaluating at least one evaluation item on the basis of the extraction result AS of the anatomical structures to evaluate whether the positioning of the object is good or bad. In this embodiment, the positioning evaluation unit 66 quantitatively evaluates whether the positioning of the left and right breasts N is good or bad. The evaluation items include at least one of the left-right symmetry of the breast, the laterality of the nipple, the pectoralis major muscle, a retromammary space, an inframammary region, or the extensibility of the mammary gland.

Specifically, the positioning evaluation unit 66 scores each evaluation item to evaluate whether the positioning is good or bad as described below. The following positioning evaluation method is known, for example, in JP2010-051456A.

Left-Right Symmetry of Breast

Each of the symmetry of the entire breast, the symmetry of the mammary gland, and the symmetry of the pectoralis major muscle is evaluated, and the left-right symmetry of the breast is evaluated by the total score of the evaluation items. In a case in which the positioning of the left and right breasts is the same, the areas of each structure in the left and right breast images will be almost equal to each other. Therefore, the symmetry of each of the entire breast, the mammary gland, and the pectoralis major muscle is evaluated on the basis of the area ratio of each structure in the left and right breast images.

Laterality of Nipple

The laterality of the nipple is evaluated on the basis of whether or not the nipple portion can be detected from the breast image. Specifically, the evaluation score is calculated on the basis of the degree of detection of the nipple portion. Evaluation is performed on each of the left and right breasts, and the laterality of the nipple is evaluated on the basis of the total score.

Pectoralis Major Muscle

Each of the position, shape, and area of a lower end portion of the pectoralis major muscle is evaluated, and the pectoralis major muscle is evaluated on the basis of the total score of the evaluation items. It is desirable that the lower end portion of the pectoralis major muscle is captured so as to be positioned up to the height of the nipple. Therefore, a position evaluation point related to the position of the lower end portion of the pectoralis major muscle is calculated on the basis of the positions of the lower end portion of the pectoralis major muscle and the nipple portion.

Further, it is desirable that the shape of the pectoralis major muscle is a convex shape. Since the shape of the pectoralis major muscle can be expressed by a quadratic function, it is possible to determine whether the shape of the pectoralis major muscle is a convex shape or a concave shape with respect to the chest wall on the basis of coefficients of the quadratic function. The shape evaluation point is calculated on the basis of the degree of unevenness of the pectoralis major muscle.

Further, it is desirable that the area of the pectoralis major muscle is in the range of 10% to 50% of the area of the entire breast. Therefore, the area evaluation point is calculated on the basis of whether or not the area of the pectoralis major muscle is within the above range.

Then, the total score obtained by adding the evaluation points of the position evaluation point, the shape evaluation point, and the area evaluation point is used as the evaluation point of the pectoralis major muscle.

Retromammary Space

The retromammary space is an evaluation item that indicates whether the entire mammary gland is visualized. The retromammary space is evaluated by analyzing whether fat is visualized behind the mammary gland. Specifically, the retromammary space is evaluated on the basis of the degree of overlap between the boundary of the pectoralis major muscle and the mammary gland. The evaluation points are calculated for each of the left and right breasts, and the retromammary space is evaluated on the basis of the total points of the evaluation points.

Inframammary Region

The inframammary region is evaluated on the basis of the shape of the breast. Specifically, the inframammary region is evaluated on the basis of whether or not the skin line reaches the lower end of the image. In a case in which the skin line reaches the lower end of the image, the evaluation points are 2. In a case in which the skin line does not reach the lower end of the image, the evaluation points are 0. The evaluation points are calculated for each of the left and right breasts, and the inframammary region is evaluated on the basis of the total points of the evaluation points.

Extensibility of Mammary Gland

The extensibility of the mammary gland is evaluated by calculating the area ratio of the mammary gland region to the entire breast (hereinafter, referred to as a mammary gland ratio) and an inframammary contrast value. The evaluation points are calculated for each of the left and right breasts, and the extensibility of the mammary gland is evaluated on the basis of the total points of the evaluation values.

Since a specific method for calculating the evaluation points of the above-mentioned evaluation items is known in JP2010-051456A, the description of a detailed method for calculating the evaluation points will be omitted.

Comprehensive Evaluation

The positioning evaluation unit 66 evaluates whether the positioning of the left and right breasts N is good or bad on the basis of the total score obtained by adding the evaluation points of the plurality of evaluation items. For example, the evaluation points of the evaluation items of the left-right symmetry of the breast, the laterality of the nipple, the pectoralis major muscle, the retromammary space, the inframammary region, and the extensibility of the mammary gland are expressed on a scale of one to ten. The positioning evaluation unit 66 calculates the total evaluation value by adding deduction points obtained by subtracting the evaluation points from the perfect score for each evaluation item. Then, the positioning evaluation unit 66 classifies the calculated total evaluation value into one of five evaluation ranks A to E.

FIG. 12 illustrates an example of the evaluation points for each evaluation item. In the example illustrated in FIG. 12, a total evaluation value S obtained by adding the deduction points of each evaluation item is "−12.5".

FIG. 13 illustrates an example of a classification table for calculating the evaluation rank on the basis of the total evaluation value S. In the classification table illustrated in FIG. 13, the numerical range of the total evaluation value S is divided into five numerical ranges, and the evaluation ranks A to E are associated with the five divided numerical ranges. The evaluation rank A indicates the highest positioning accuracy. The evaluation rank E indicates the lowest positioning accuracy. The positioning evaluation unit 66 calculates the evaluation rank on the basis of the classification table illustrated in FIG. 13. In a case in which the total evaluation value S is "−12.5", the evaluation rank is "C".

The positioning evaluation unit 66 outputs a result PE of evaluating whether positioning is good or bad to the display processing unit 67. In this embodiment, the evaluation result PE includes the evaluation points of each evaluation item, the total evaluation value S, and the evaluation rank. In addition, the evaluation result PE may include any one of the evaluation score, the total evaluation value S, or the evaluation rank.

Figure 14:
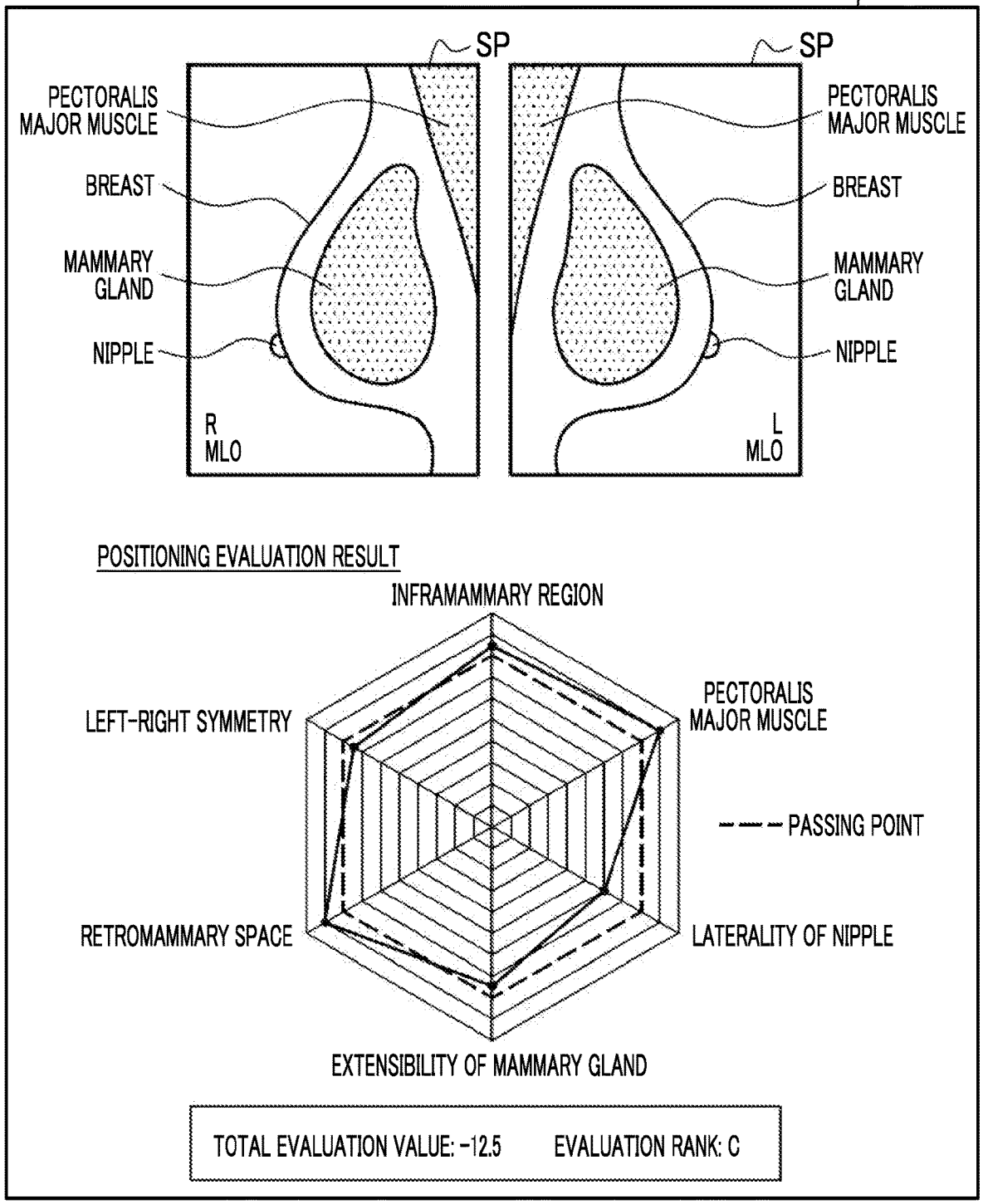
FIG. 14 is a diagram illustrating an example of the display of the result of evaluating whether positioning is good or bad.

In a case in which the display processing unit 67 receives the result PE of evaluating whether the positioning is good or bad from the positioning evaluation unit 66, the display processing unit 67 displays the evaluation result PE together with the synthesized two-dimensional image SP on the display unit 21. For example, as illustrated in FIG. 14, the display processing unit 67 displays the evaluation points of each evaluation item as a so-called radar chart. Further, the display processing unit 67 displays the total evaluation value S and the evaluation rank. In addition, a dashed line in the radar chart indicates a line of passing points (8 points) of the evaluation points.

The radiographer can quantitatively and intuitively understand whether the positioning of the left and right breasts N is good or bad from the evaluation result PE displayed on the display unit 21 as illustrated in FIG. 14.

In addition, the display format of the evaluation result PE displayed on the display unit 21 is not limited to the example illustrated in FIG. 14. The display processing unit 67 may display a warning that prompts the radiographer to perform reimaging on the display unit 21 in a case in which the positioning is not proper. Further, the warning that prompts the radiographer to perform reimaging may be issued as a voice message from a speaker (not illustrated).

As described above, in this embodiment, the anatomical structure extraction process is performed on the basis of the selected image XS selected from the plurality of projection images XP obtained by the tomosynthesis imaging, instead of the synthesized two-dimensional image SP. Therefore, the anatomical structure extraction process can be started without waiting for the completion of the synthesis process of generating the synthesized two-dimensional image SP. In this embodiment, the control unit 50 of the console 20 starts the anatomical structure extraction process before or during the synthesis process. Specifically, it is preferable that the control unit 50 starts the anatomical structure extraction process before the reconstruction process is performed.

Figure 15:
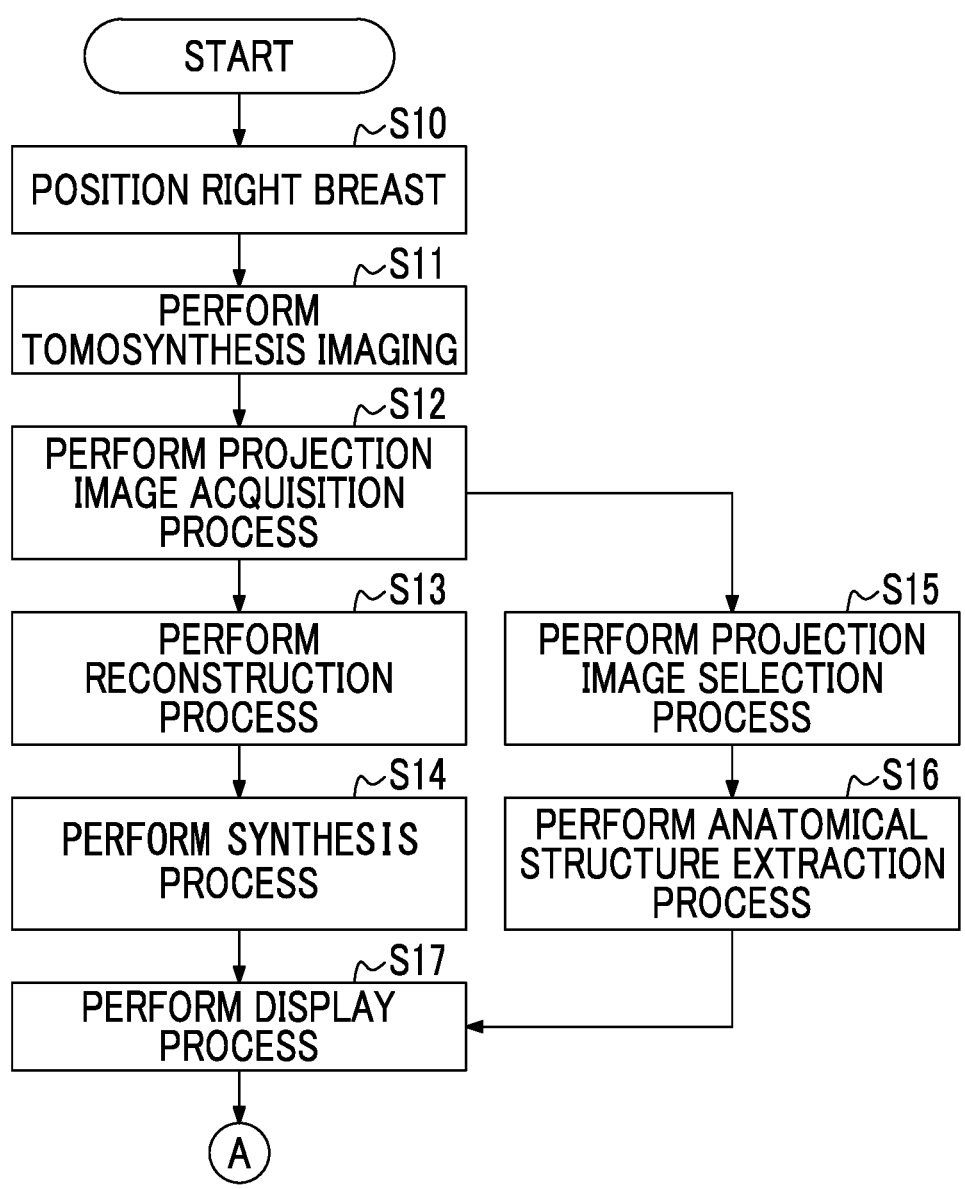
FIG. 15 is a flowchart illustrating an example of a processing procedure in a case in which the tomosynthesis imaging is performed on a right breast.
Figure 16:
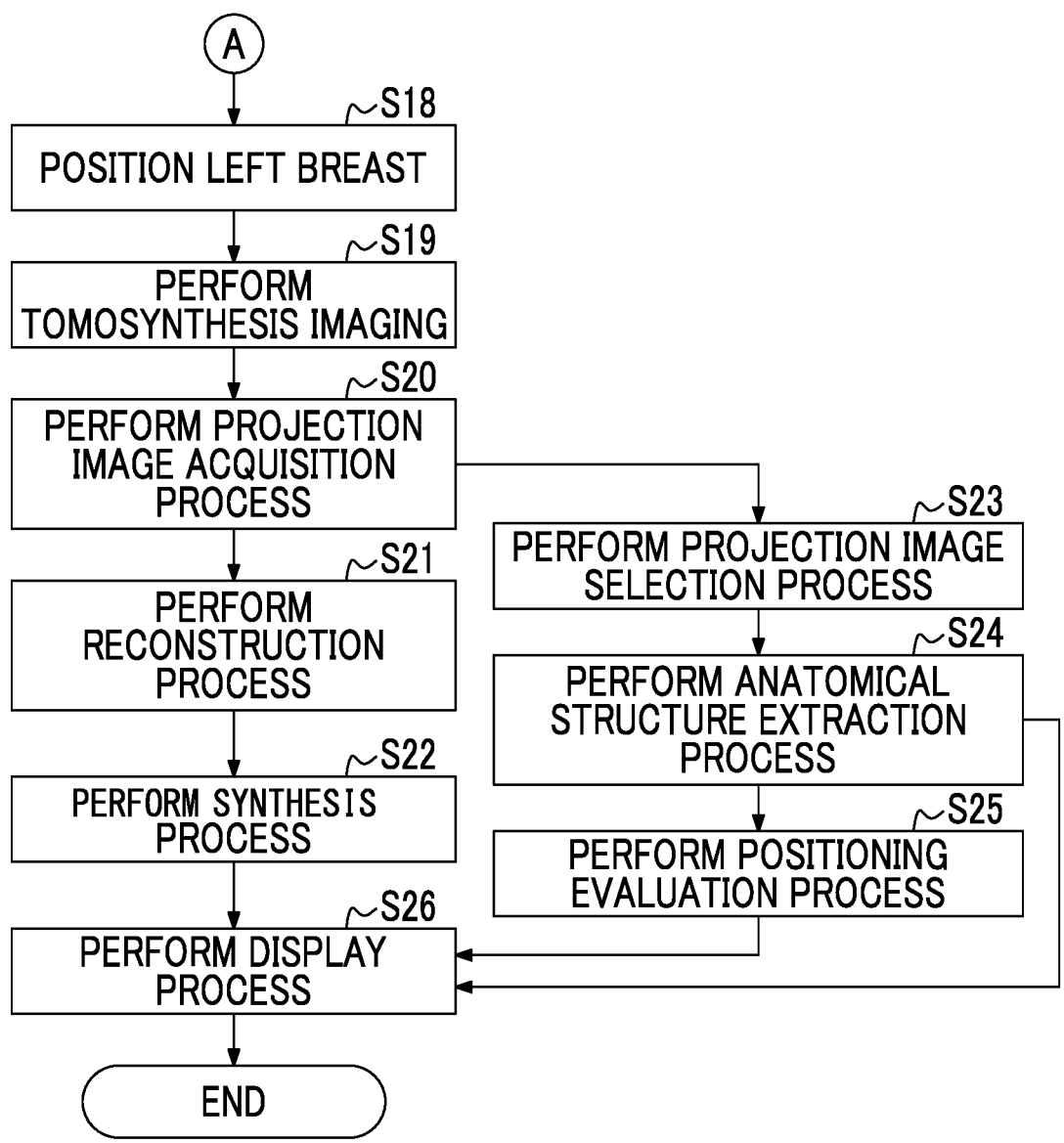
FIG. 16 is a flowchart illustrating an example of a processing procedure in a case in which the tomosynthesis imaging is performed on a left breast.

Next, the operation of the above-mentioned configuration will be described with reference to flowcharts illustrated in FIGS. 15 and 16. FIG. 15 illustrates an example of a processing procedure in a case in which the tomosynthesis imaging is performed on the right breast N of the subject W. FIG. 16 illustrates an example of a processing procedure in a case in which the tomosynthesis imaging is performed on the left breast N of the subject W.

First, the radiographer performs a preparatory operation of setting the state of the mammography apparatus 10 according to the designated imaging method (for example, the MLO imaging or the CC imaging). After the preparatory operation is completed, the radiographer guides the subject W to the mammography apparatus 10 and starts the positioning of the breast N. After placing the breast N on the imaging table 13, the radiographer operates a compression plate movement switch (not illustrated) to compress the breast N with the compression plate 14.

For example, first, the radiographer positions the right breast N of the subject W using the above-mentioned method (Step S10). In a case in which the positioning is completed, the radiographer operates an exposure switch (not illustrated) to direct the mammography apparatus 10 to perform the tomosynthesis imaging (Step S11). The plurality of projection images XP obtained by the tomosynthesis imaging are transmitted to the console 20.

In the console 20, the projection image acquisition unit 61 performs the projection image acquisition process of acquiring the plurality of projection images XP transmitted from the mammography apparatus 10 (Step S12). The plurality of projection images XP acquired by the projection image acquisition unit 61 are stored in the storage unit 52.

Then, the reconstruction unit 62 performs the reconstruction process (see FIG. 6) on the basis of the plurality of projection images XP stored in the storage unit 52 (Step S13). The synthesis unit 63 performs the synthesis process (see FIG. 7) on the basis of the plurality of tomographic images TP generated by the reconstruction process (Step S14). The synthesized two-dimensional image SP is generated as the projection image based on the virtual radiation source position PK by the synthesis process.

After the projection image acquisition unit 61 performs the projection image acquisition process in Step S12, the selection unit 64A included in the anatomical structure extraction unit 64 performs the projection image selection process (FIGS. 8 and 9) in parallel to the reconstruction process (Step S15). The selection unit 64A specifies a radiation source position closest to the virtual radiation source position PK from the plurality of radiation source positions P1 to P5 and selects the projection image XP corresponding to the specified radiation source position as the selected image XS. Then, the extraction unit 64B performs the anatomical structure extraction process (see FIG. 10) of extracting the anatomical structures on the basis of the selected image XS (Step S16).

After Step S14 and Step S16, the display processing unit 67 performs the display process of displaying the extraction result AS of the anatomical structures by the anatomical structure extraction process on the display unit 21 together with the synthesized two-dimensional image SP generated by the synthesis process (Step S17).

Then, the radiographer positions the left breast N of the subject W (Step S18). In a case in which the positioning is completed, the radiographer operates the exposure switch to direct the mammography apparatus 10 to perform the tomosynthesis imaging (Step S19). Then, the same process as described above is performed. Since Steps S20 to S24 illustrated in FIG. 16 are the same processes as Steps S12 to S16 illustrated in FIG. 15, the description thereof will not be repeated.

In a case in which Step S24 is completed, the positioning evaluation unit 66 performs the positioning evaluation process on the basis of a plurality of evaluation items (see FIG. 12), using the extraction result AS of the anatomical structures by the anatomical structure extraction process in Step S16 and Step S24 (Step S25). In Step S25, it is evaluated whether the positioning of the left and right breasts N is good or bad.

After Step S22 and Step S25, the display processing unit 67 performs the display process (see FIG. 14) of displaying the result PE of evaluating whether the positioning is good or bad on the display unit 21 together with the synthesized two-dimensional image SP in addition to the extraction result AS of the anatomical structures (Step S26).

The radiographer can easily determine whether or not the positioning of the left and right breasts N is proper on the basis of the extraction result AS of the anatomical structures and the result PE of evaluating whether the positioning is good or bad, which are displayed on the display unit 21. In a case in which the radiographer determines that the positioning is not proper, the radiographer optimizes the positioning and performs reimaging.

As described above, according to the technology of the present disclosure, it is possible to evaluate whether the positioning of the object is good or bad, without using the synthesized two-dimensional image. In a case in which the positioning is evaluated using the synthesized two-dimensional image, it is necessary to re-optimize the process whenever either the reconstruction process or the synthesis process is changed, which is complicated. However, according to the technology of the present disclosure, the complexity is removed.

In addition, according to the technology of the present disclosure, the anatomical structure extraction process can be started before or during the synthesis process. Therefore, it is possible to shorten the time until the extraction result of the anatomical structures is obtained from the start of the tomosynthesis imaging. As a result, the radiographer can determine whether the positioning is good or bad at an early stage.

Modification Examples

Next, various modification examples of the above-described embodiment will be described.

In the above-described embodiment, the display processing unit 67 displays the extraction result AS of the anatomical structures on the display unit 21 (see FIGS. 11 and 14). The extraction result AS is information indicating the characteristics (for example, the position, shape, and size) of the anatomical structures. Further, the display processing unit 67 may display the values measured on the basis of the extraction result AS of the anatomical structures on the display unit 21. The measured values displayed on the display unit 21 by the display processing unit 67 are measured values related to the position, shape, or size of the anatomical structures. These measured values may be the measured values of the anatomical structures measured in a case in which the positioning evaluation unit 66 calculates the evaluation points for each evaluation item on the basis of the extraction result AS of the anatomical structures.

Figure 17:
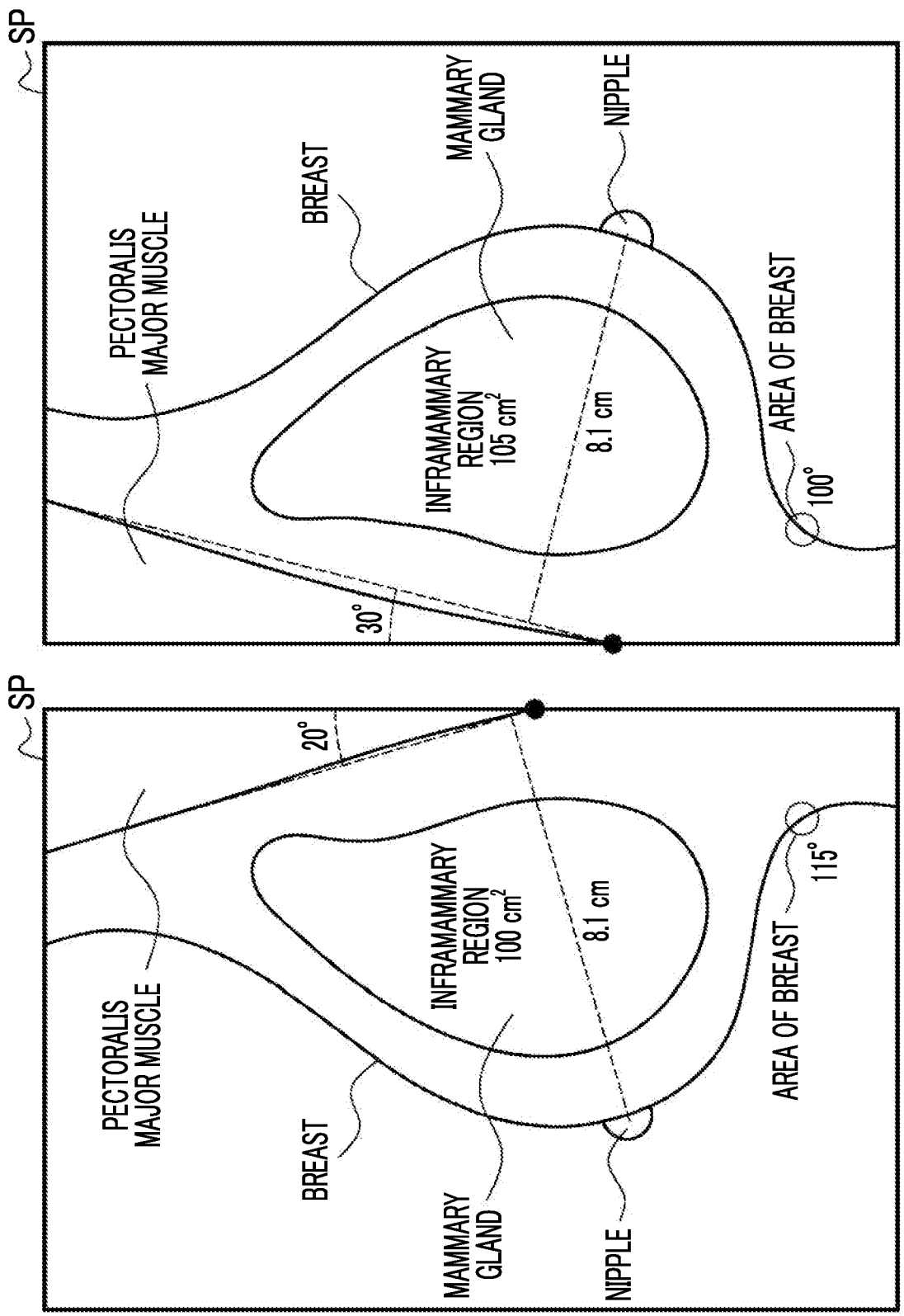
FIG. 17 is a diagram illustrating an example of measured values displayed on a display unit.

FIG. 17 illustrates an example of the measured values displayed on the display unit 21. For example, the display processing unit 67 displays a distance between the breast and the pectoralis major muscle, the area of the breast, the angle of the pectoralis major muscle, and the angle of the inframammary region on the display unit 21. Further, in a case in which there is a difference in height between the left and right breasts, the display processing unit 67 may display the measured value of the difference in height on the display unit 21.

Furthermore, in the above-described embodiment, the display unit 21 is a display device provided in the console 20. However, the display unit 21 may be a display device that is provided separately from the console 20. For example, the display unit 21 may be a display device that is provided in a computer connected to the console 20 through a network.

Moreover, in the above-described embodiment, the display processing unit 67 displays the extraction result AS of the anatomical structures and the result PE of evaluating whether the positioning is good or bad together with the synthesized two-dimensional image SP. However, the display processing unit 67 may further display the tomographic image TP.

In addition, in the above-described embodiment, the extraction unit 64B extracts the anatomical structures on the basis of the selected image XS. However, the extraction unit 64B may extract the anatomical structures using one or more tomographic images TP in addition to the selected image XS. Further, in a case in which the anatomical structure extraction process is started before or during the reconstruction process, the extraction unit 64B may start the anatomical structure extraction process on the basis of the tomographic image TP at the time when at least one tomographic image TP is obtained by the reconstruction process. In this case, the extraction unit 64B may update the extraction result AS of the anatomical structures extracted on the basis of the selected image XS, using the extraction result of the anatomical structures extracted on the basis of the tomographic image TP. Here, the update means the overwriting of information or the addition of information.

Furthermore, in the above-described embodiment, the mammography apparatus 10 moves the radiation source 16 in order to emit radiation at a plurality of radiation source positions in the tomosynthesis imaging. Instead of this, a radiation source (see, for example, JP2020-048978A) may be used which has a plurality of radiation tubes disposed at positions corresponding to the plurality of radiation source positions. In this case, radiation may be emitted while the radiation source is fixed and the plurality of radiation tubes are switched one by one.

Moreover, in the above-described embodiment, the technology of the present disclosure has been described using the mammography apparatus 10 as an example of the radiography apparatus. The radiography apparatus according to the technology of the present disclosure is not limited to the mammography apparatus and may be a radiography apparatus that images parts other than the breast. Therefore, the anatomical structures extracted by the extraction unit 64B are not limited to the structures included in the breast. For example, in a case in which the imaging part is the chest, the extraction unit 64B extracts the lung field, the heart, and the like as the anatomical structures. In this case, the positioning evaluation unit 66 may evaluate whether the positioning is good or bad, using the area of the lung field, the inclination of each of the left and right lung field regions, and the like as the evaluation items. That is, the positioning evaluation unit 66 may perform the positioning evaluation process on the basis of the anatomical structures extracted from one selected image XS.

In addition, in the above-described embodiment, the anatomical structure extraction unit 64 selects, as the selected image XS, the projection image XP corresponding to the radiation source position closest to a preset virtual radiation source position PK from the plurality of projection images XP acquired at the plurality of radiation source positions. Instead of this, one projection image XP suitable for diagnosis may be selected from the plurality of projection images XP acquired at the plurality of radiation source positions, and the radiation source position where the selected projection image XP is acquired may be used as the virtual radiation source position PK.

Figure 18:
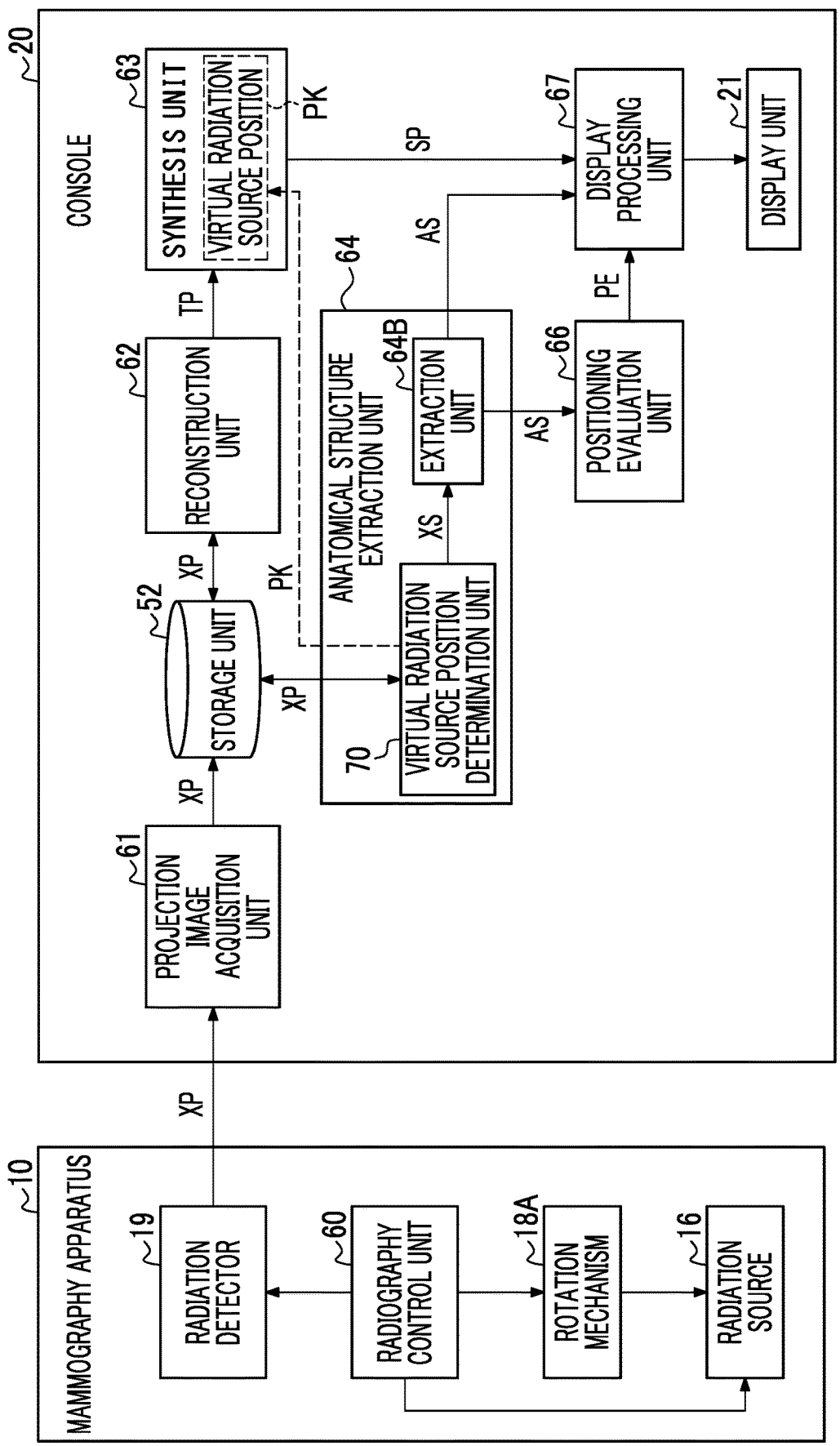
FIG. 18 is a block diagram illustrating a modification example of an anatomical structure extraction unit.

FIG. 18 illustrates a modification example of the anatomical structure extraction unit 64. An anatomical structure extraction unit 64 according to this modification example has a virtual radiation source position determination unit 70 instead of the selection unit 64A according to the above-described embodiment. The virtual radiation source position determination unit 70 selects one projection image XP suitable for diagnosis from the plurality of projection images XP stored in the storage unit 52 and determines the radiation source position where the selected projection image XP has been acquired as the virtual radiation source position PK.

The virtual radiation source position determination unit 70 inputs the determined virtual radiation source position PK to the synthesis unit 63 and inputs the selected projection image XP as the selected image XS to the extraction unit 64B.

In this modification example, the synthesis unit 63 performs a synthesis process of generating the synthesized two-dimensional image SP on the basis of the virtual radiation source position PK input from the virtual radiation source position determination unit 70. The extraction unit 64B extracts the anatomical structures from the selected image XS input from the virtual radiation source position determination unit 70. Therefore, in this modification example, the virtual radiation source position determination unit 70 performs the virtual radiation source position determination process before the synthesis process is performed.

The anatomical structure extraction process according to this modification example is preferably applied to a radiography system for diagnosing a knee joint of the subject. Osteoarthritis of the knee is one of the diseases of the knee joint. As the osteoarthritis of the knee progresses, the cartilage between the femur and the tibia wears down, and a gap (for example, a joint space) between the femur and the tibia is reduced. The osteoarthritis of the knee is diagnosed by measuring the width of the joint space on the basis of the radiographic images.

Since the width of the joint space is very small, it is necessary to accurately position the knee joint of the subject in order to diagnose the joint space. It is preferable to appropriately rotate the knee joint inward during positioning. However, in a case in which the positioning is improper, imaging is performed in a state in which the femur and the tibia overlap each other. In this case, it is difficult to diagnose the joint space.

Figure 19:
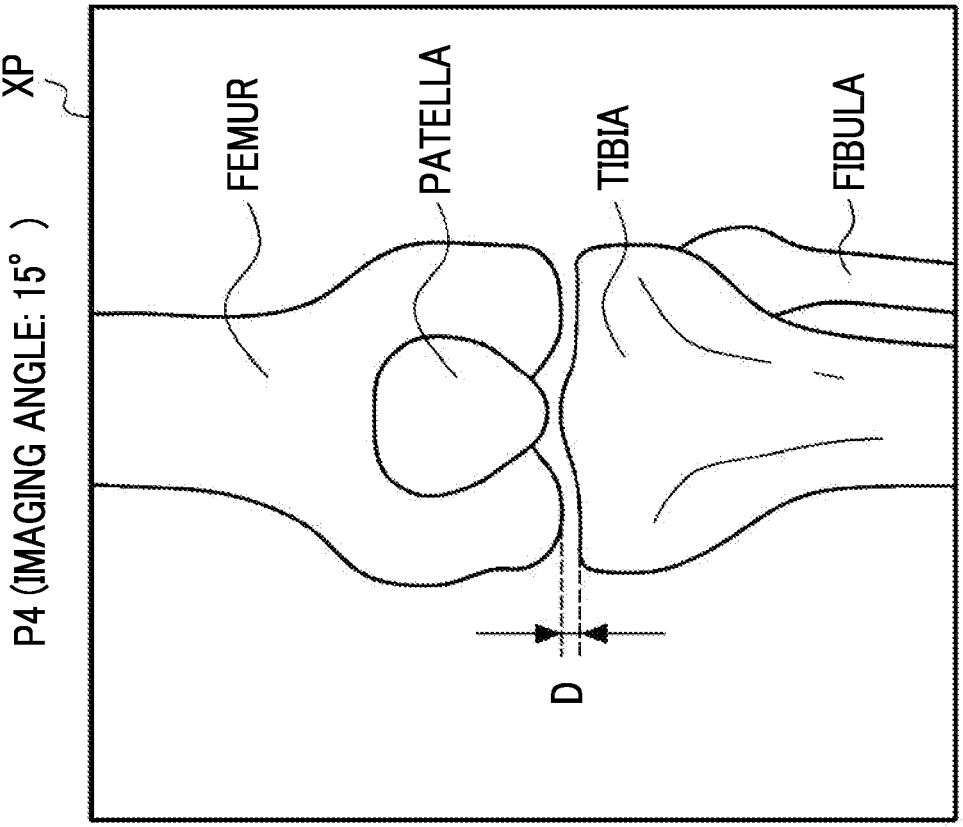
FIG. 19 is a diagram illustrating the dependence of a joint space on an imaging angle.
Figure 19:
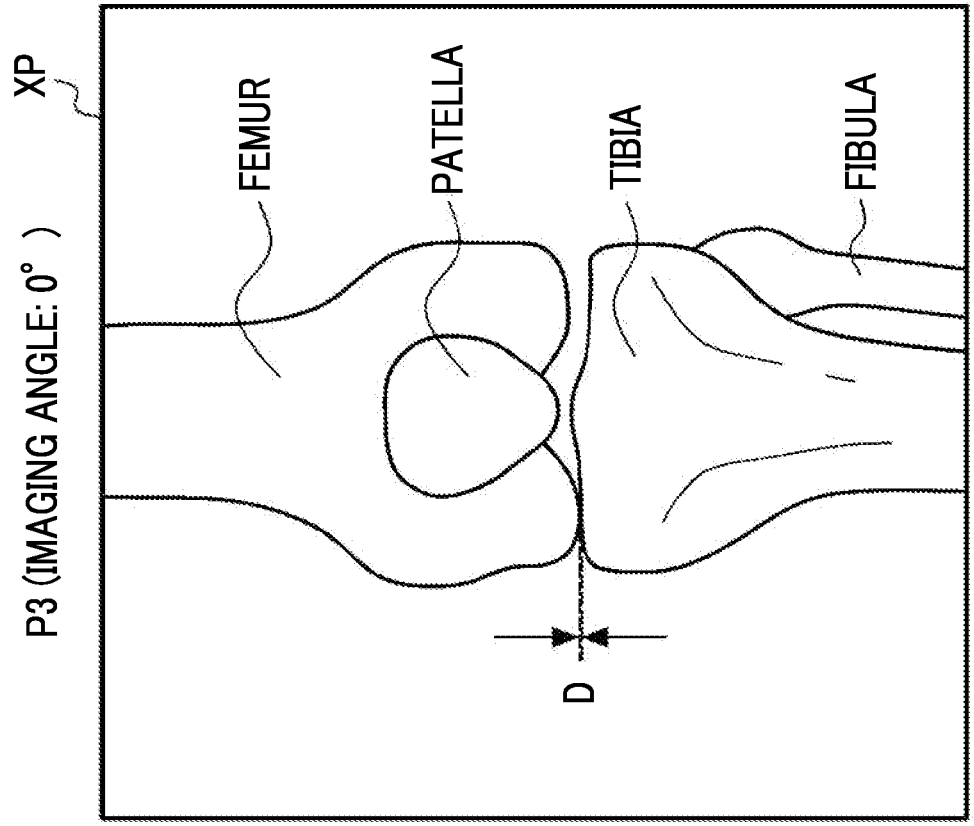

In the tomosynthesis imaging, radiography is performed while changing the imaging angle (that is, changing the radiation source position). Therefore, the joint space may be difficult to see depending on the imaging angle. FIG. 19 illustrates the imaging angle dependence of the joint space in the projection image XP obtained by the tomosynthesis imaging. FIG. 19 illustrates an example of the projection images XP obtained at the radiation source positions P3 and P4 (see FIG. 3). D indicates a minimum width of the joint space (hereinafter, referred to as a minimum space width). In the example illustrated in FIG. 19, the minimum space width D in the case of the radiation source position P4 corresponding to an imaging angle of 15° is larger than that in the case of the radiation source position P3 corresponding to an imaging angle of 0°. As described above, the case in which the imaging angle is not 0° may be more suitable for diagnosing the joint space.

Figure 20:
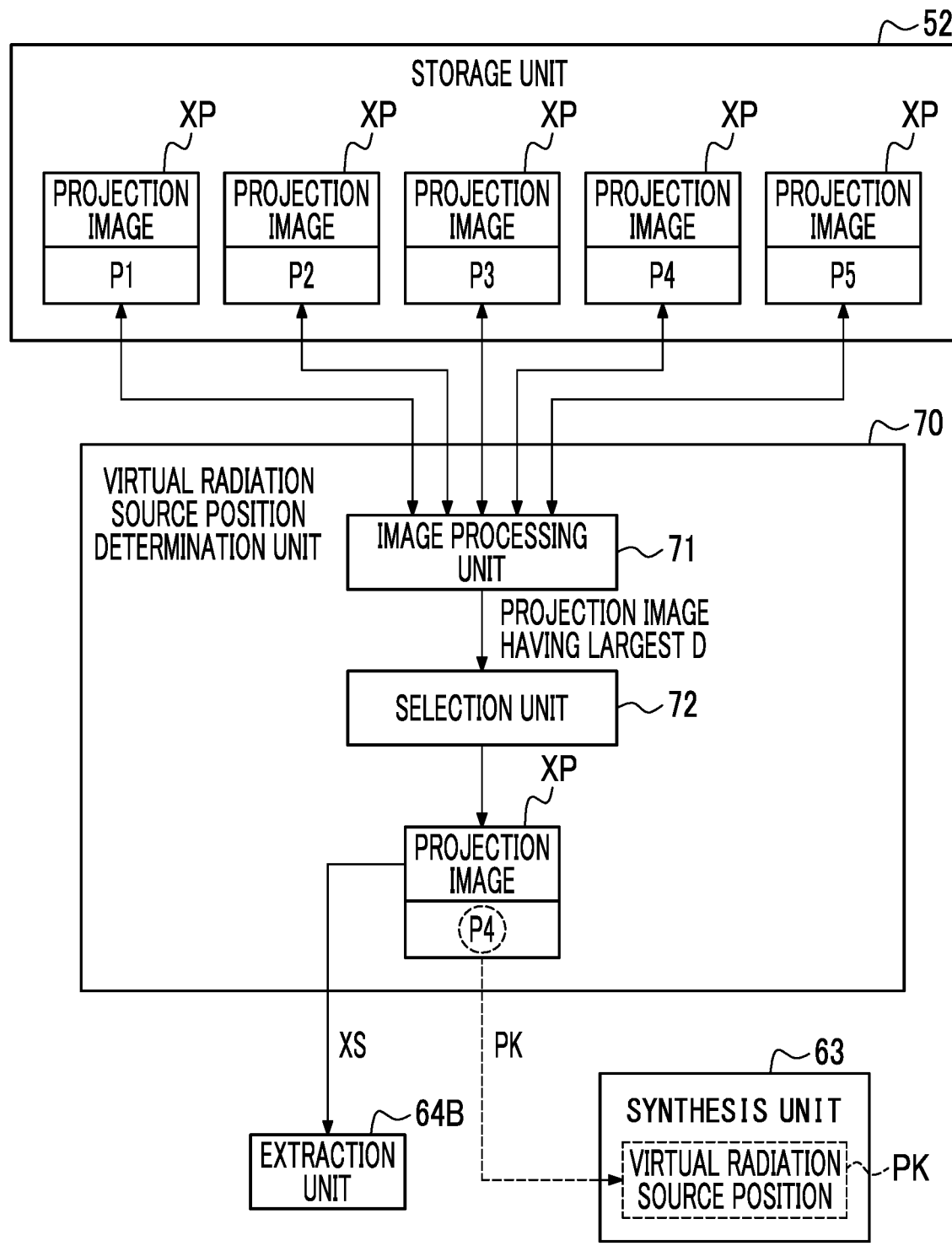
FIG. 20 is a block diagram illustrating an example of a configuration of a virtual radiation source position determination unit.

FIG. 20 illustrates an example of the configuration of the virtual radiation source position determination unit 70. The virtual radiation source position determination unit 70 includes an image processing unit 71 and a selection unit 72. The image processing unit 71 analyzes a plurality of projection images XP stored in the storage unit 52 and measures the minimum space width D for each of the projection images XP. For example, the image processing unit 71 detects the contour line of each of the femur and the tibia and measures the minimum width between the contour line of the femur and the contour line of the tibia as the minimum space width D.

The image processing unit 71 analyzes the projection images XP using a machine learning method, such as deep learning, to extract each region of the femur, the tibia, and the patella and specifies the contour line of the femur and the contour line of the tibia on the basis of each extracted region. Then, the image processing unit 71 measures the minimum width between the contour line of the femur and the contour line of the tibia to calculate the minimum space width D.

The selection unit 72 selects the projection image XP having the largest minimum space width D on the basis of the measurement result of the minimum space width D by the image processing unit 71. In the example illustrated in FIG. 20, the selection unit 72 selects the projection image XP corresponding to the radiation source position P4. The radiation source position P4 where the projection image XP selected by the selection unit 72 has been acquired is determined as the virtual radiation source position PK and is input to the synthesis unit 63. Further, the projection image XP corresponding to the radiation source position P4 is input as the selected image XS to the extraction unit 64B.

Figure 21:
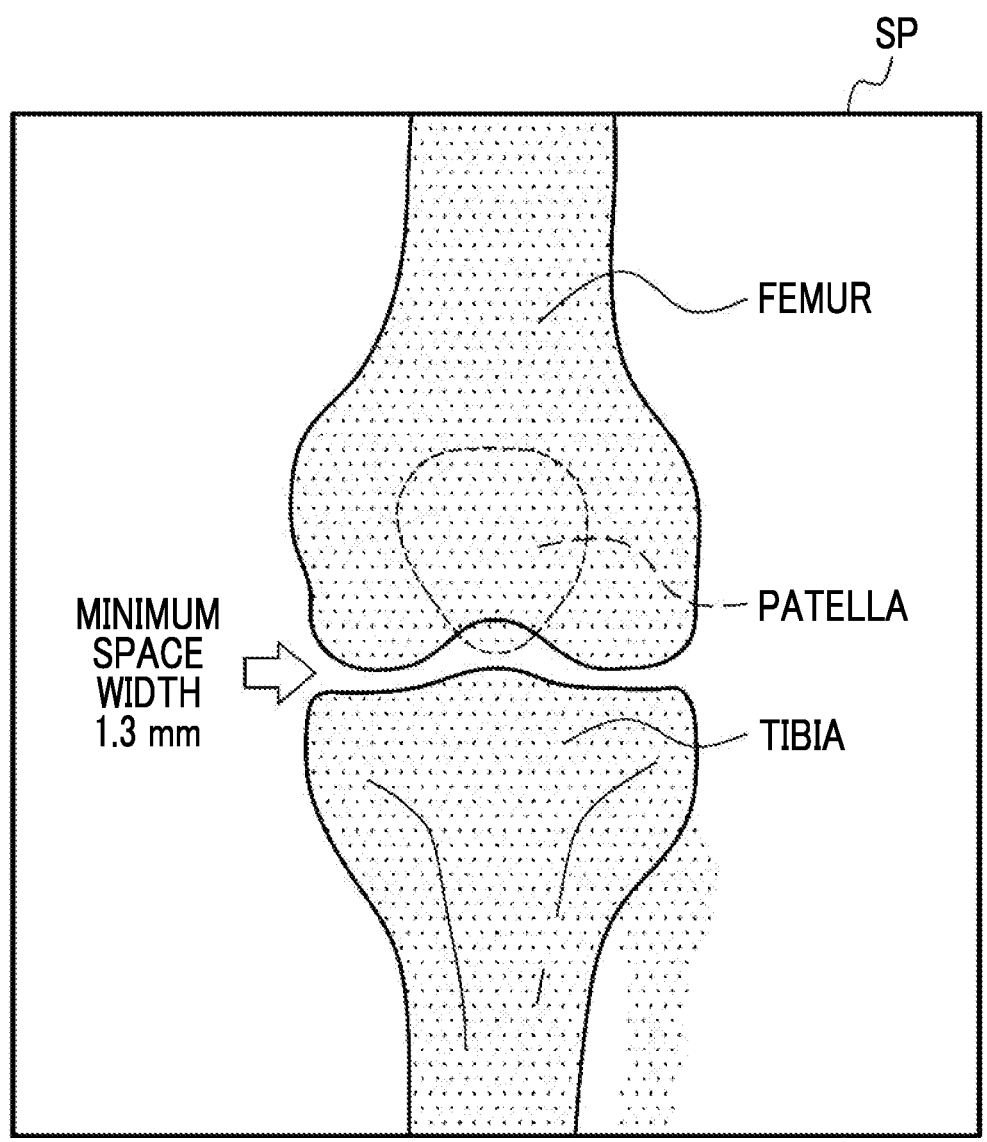
FIG. 21 is a diagram illustrating an example of anatomical structures extracted from a selected image XS by an extraction unit according to a modification example.

FIG. 21 illustrates an example of the anatomical structures extracted from the selected image XS by the extraction unit 64B according to this modification example. In this modification example, the extraction unit 64B extracts, for example, the femur, the tibia, and the patella as the anatomical structures. Further, in this modification example, the display processing unit 67 displays the contour line of each of the femur and the tibia on the display unit 21 together with the synthesized two-dimensional image SP. Furthermore, the display processing unit 67 may display the measured value of the minimum space width D measured by the image processing unit 71 on the display unit 21 together with the synthesized two-dimensional image SP.

Figure 22:
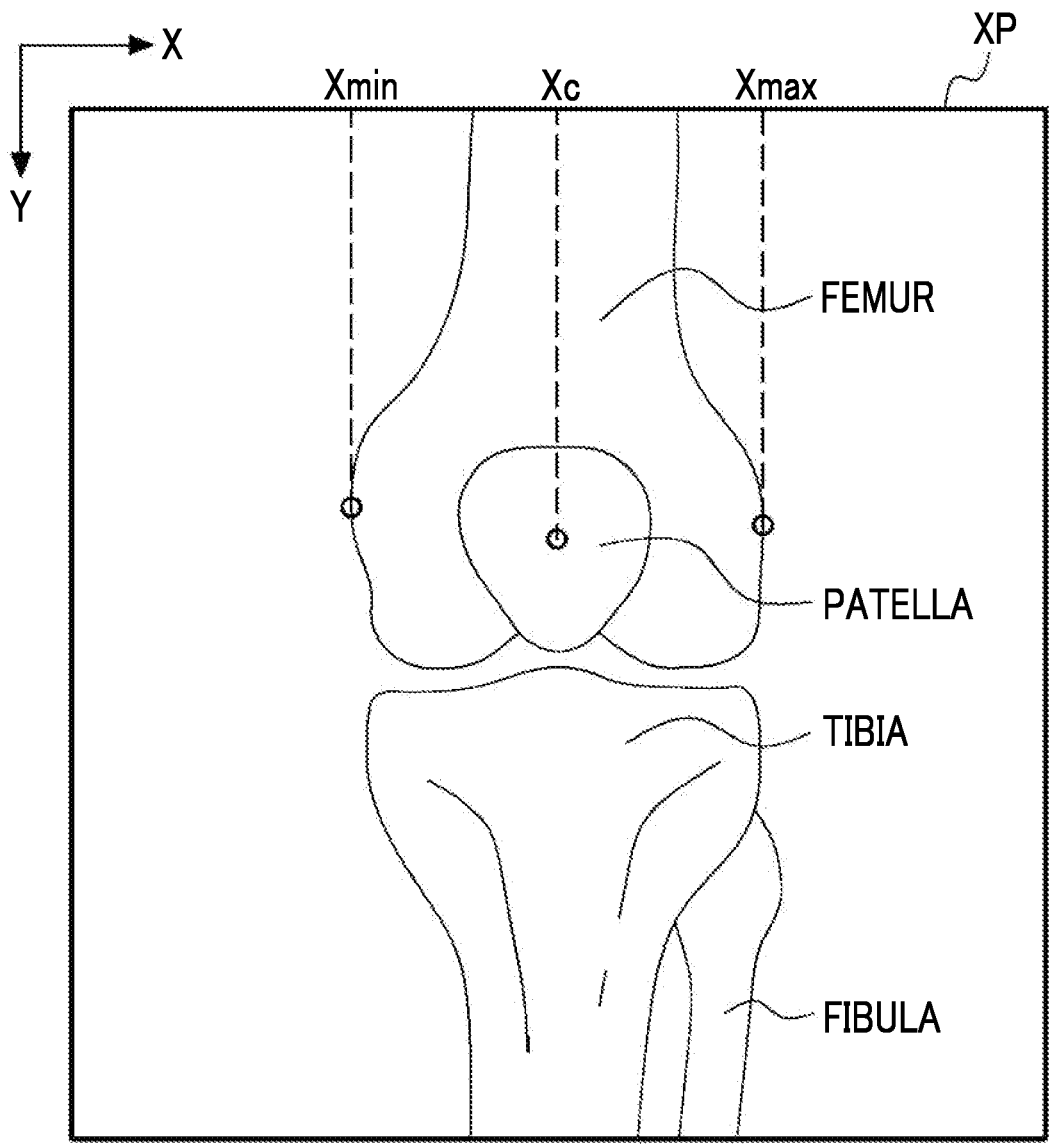
FIG. 22 is a diagram illustrating an example of a positioning evaluation process according to a modification example.
Figure 22:
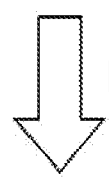

FIG. 22 illustrates an example of the positioning evaluation process according to this modification example. In this modification example, the positioning evaluation unit 66 evaluates positioning on the basis of the position of the patella with respect to the region of the femur. Specifically, it is assumed that the center coordinates of the patella in one direction (the X-axis direction in FIG. 22) are Xc, the maximum coordinates of the femur in the one direction are Xmax, and the minimum coordinates of the femur in the one direction are Xmin. For example, the positioning evaluation unit 66 evaluates the positioning of the knee joint on the basis of an evaluation value S represented by the following Expression (1).

$$S = |0.5 - Xc/(X\max + X\min)| \quad (1)$$

The accuracy of the positioning of the knee joint increases as the patella is located in the region of the femur. That is, as the evaluation value S becomes closer to 0, the accuracy of the positioning becomes higher. The positioning evaluation unit 66 may generate a positioning evaluation rank on the basis of the evaluation value S as in the above-described embodiment. The display processing unit 67 displays at least one of the evaluation value S or the evaluation rank as the result of evaluating whether the positioning is good or bad on the display unit 21.

Figure 23:
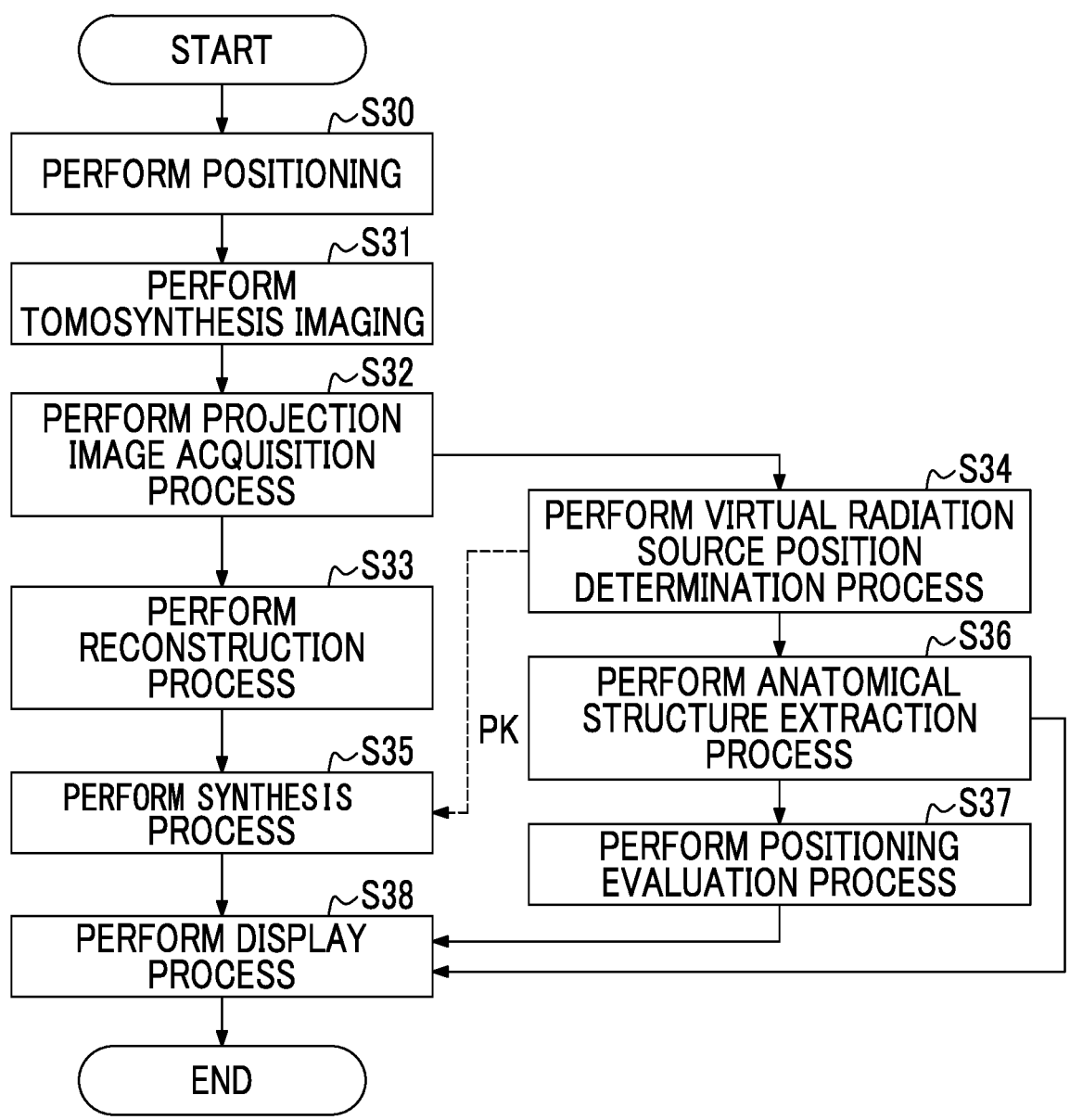
FIG. 23 is a flowchart illustrating the operation of a radiography system according to a modification example.

FIG. 23 is a flowchart illustrating the operation of the radiography system according to this modification example. First, the radiographer positions the knee joint of the subject with respect to the radiography apparatus (Step S30). In a case in which the positioning is completed, the radiographer operates the exposure switch to direct the radiography apparatus to perform the tomosynthesis imaging (Step S31).

A projection image acquisition process (Step S32) and a reconstruction process (Step S33) are the same as those in Steps S12 and S13 (see FIG. 15) in the above-described embodiment. After Step S32, the virtual radiation source position determination unit 70 selects one projection image XP suitable for diagnosis from a plurality of projection images XP acquired by the projection image acquisition process and determines the radiation source position, where the selected projection image XP has been acquired, as the virtual radiation source position PK (Step S34).

This virtual radiation source position determination process is performed in parallel to the reconstruction process. The virtual radiation source position PK determined by the virtual radiation source position determination process is input to the synthesis unit 63. In addition, the projection image XP selected by the virtual radiation source position determination process is input as the selected image XS to the extraction unit 64B.

In a case in which the reconstruction process ends and the virtual radiation source position PK is input from the virtual radiation source position determination unit 70, the synthesis unit 63 generates the synthesized two-dimensional image SP on the basis of the input virtual radiation source position PK (Step S35). On the other hand, the extraction unit 64B extracts the anatomical structures from the selected image XS input from the virtual radiation source position determination unit 70 (Step S36).

After Step S35 and Step S37, the display processing unit 67 displays the result of evaluating whether the positioning is good or bad on the display unit 21 together with the synthesized two-dimensional image SP in addition to the extraction result of the anatomical structures (Step S38).

Figure 24:
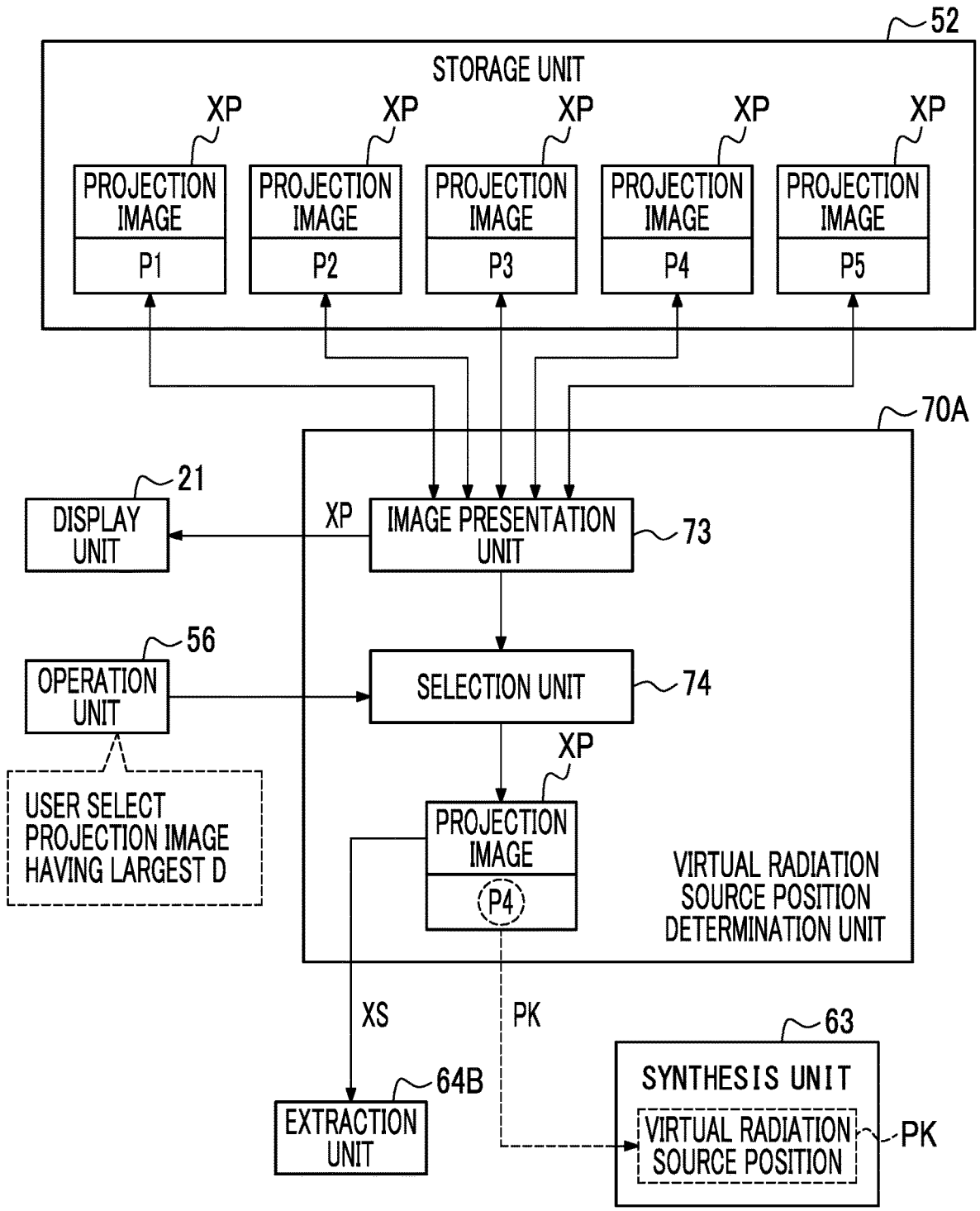
FIG. 24 is a block diagram illustrating a modification example of the virtual radiation source position determination unit.

FIG. 24 illustrates a modification example of the virtual radiation source position determination unit 70. A virtual radiation source position determination unit 70A according to this modification example includes an image presentation unit 73 and a selection unit 74. The image presentation unit 73 displays the plurality of projection images XP stored in the storage unit 52 on the display unit 21. After observing the plurality of projection images XP displayed on the display unit 21, the user (for example, the radiographer) operates the operation unit 56 to select the projection image XP having the largest minimum space width D. In this modification example, the user selects, for example, the projection image XP corresponding to the radiation source position P4.

The selection unit 74 inputs the projection image XP selected by the user through the operation unit 56 as the selected image XS to the extraction unit 64B. In addition, the selection unit 74 inputs the radiation source position, where the selected projection image XP has been acquired, as the virtual radiation source position PK to the synthesis unit 63.

As described above, the virtual radiation source position determination unit 70A according to this modification example determines the virtual radiation source position PK on the basis of one projection image XP suitable for the diagnosis which has been selected by the user.

In the above-described embodiment, for example, the following various processors can be used as the hardware structure of processing units performing various processes such as the radiography control unit 60, the projection image acquisition unit 61, the reconstruction unit 62, the synthesis unit 63, the anatomical structure extraction unit 64, the positioning evaluation unit 66, and the display processing unit 67.

The various processors include, for example, a CPU, a programmable logic device (PLD), and a dedicated electric circuit. As is well known, the CPU is a general-purpose processor that executes software (programs) to function as various processing units. The PLD is a processor such as a field programmable gate array (FPGA) whose circuit configuration can be changed after manufacture. The dedicated electric circuit is a processor that has a dedicated circuit configuration designed to perform a specific process, such as an application specific integrated circuit (ASIC).

One processing unit may be configured by one of the various processors or a combination of two or more processors of the same type or different types (for example, a combination of a plurality of FPGAs and a combination of a CPU and an FPGA). Further, a plurality of processing units may be configured by one processor. A first example of the configuration in which a plurality of processing units are configured by one processor is an aspect in which one processor is configured by a combination of one or more CPUs and software and functions as a plurality of processing units. A second example of the configuration is an aspect in which a processor that implements the functions of the entire system including a plurality of processing units using one IC chip is used. A representative example of this aspect is a system on chip (SoC). As described above, various processing units are configured by one or more of the various processors as the hardware structure.

In addition, specifically, an electric circuit (circuitry) obtained by combining circuit elements, such as semiconductor elements, is used as the hardware structure of the various processors.

The present disclosure is not limited to the above-described embodiment and may adopt various configurations without departing from the gist and scope of the present disclosure. Furthermore, the present disclosure extends to a computer-readable storage medium that non-temporarily stores the program, in addition to the program.

What is claimed is:

1. An information processing device comprising:
a processor and a memory coupled to the processor,
wherein the processor is configured to execute instructions stored in the memory, to perform:
a reconstruction process of reconstructing a plurality of tomographic images from a plurality of projection images obtained by tomosynthesis imaging that irradiates an object with radiation from a radiation source at a plurality of predetermined radiation source positions;
a synthesis process of synthesizing the plurality of tomographic images to generate a synthesized two-dimensional image as a projection image based on a virtual radiation source position;
a projection image selection process of selecting a projection image corresponding to a predetermined radiation source position closest to the virtual radiation source position among the plurality of predetermined radiation source positions;
an anatomical structure extraction process of extracting anatomical structures from the selected projection image; and
a display process of displaying an extraction result of the anatomical structures on a display device together with the synthesized two-dimensional image,
wherein the virtual radiation source position is a position different from the plurality of predetermined radiation source positions or a position that coincides with one of the plurality of predetermined radiation source positions, and
wherein, in the synthesis process, the processor generates the synthesized two-dimensional image, which corresponds to a projection image in a case where the object is irradiated with radiation from the virtual radiation source position, by performing a projection process or an addition process on the plurality of tomographic images in a direction corresponding to the virtual radiation source position.

2. The information processing device according to claim 1, wherein the processor starts the anatomical structure extraction process before or during the synthesis process.

3. The information processing device according to claim 1, wherein the processor performs a positioning evaluation process of evaluating at least one evaluation item on the basis of the extraction result of the anatomical structures to evaluate whether positioning of the object is good or bad.

4. The information processing device according to claim 3, wherein the processor displays a result of evaluating whether the positioning is good or bad by the positioning evaluation process on the display device together with the synthesized two-dimensional image in the display process.

5. The information processing device according to claim 3, wherein the projection image is a breast image obtained by imaging a breast as the object.

6. The information processing device according to claim 5, wherein the anatomical structures include at least one of the breast, a mammary gland, a pectoralis major muscle, or a nipple.

7. The information processing device according to claim 6, wherein the evaluation items include at least one of a left-right symmetry of the breast, a laterality of the nipple, the pectoralis major muscle, a retromammary space, an inframammary region, or an extensibility of the mammary gland.

8. The information processing device according to claim 1, wherein the processor performs a virtual radiation source position determination process of determining the virtual radiation source position before the synthesis process.

9. The information processing device according to claim 8, wherein, in the virtual radiation source position determination process, the processor determines the virtual radiation source position on the basis of one projection image selected by analyzing the plurality of projection images.

10. The information processing device according to claim 8, wherein, in the virtual radiation source position determination process, the processor determines the virtual radiation source position on the basis of one projection image selected by a user through an operation device among the plurality of projection images.

11. A radiography system comprising:
a radiography apparatus; and
the information processing device according to claim 1, wherein the radiography apparatus acquires the plurality of projection images by irradiating the object with radiation from the radiation source at the plurality of predetermined radiation source positions.

12. The information processing device according to claim 1, wherein, in the display process, the processor displays the extraction result of the anatomical structures and the synthesized two-dimensional image in association with each other on the display device.

13. An information processing method comprising:
reconstructing a plurality of tomographic images from a plurality of projection images obtained by tomosynthesis imaging that irradiates an object with radiation from a radiation source at a plurality of predetermined radiation source positions;
synthesizing the plurality of tomographic images to generate a synthesized two-dimensional image as a projection image based on a virtual radiation source position;
selecting a projection image corresponding to a predetermined radiation source position closest to the virtual radiation source position among the plurality of predetermined radiation source positions;
extracting anatomical structures from the selected projection image; and
displaying an extraction result of the anatomical structures on a display device together with the synthesized two-dimensional image,
wherein the virtual radiation source position is a position different from the plurality of predetermined radiation source positions or a position that coincides with one of the plurality of predetermined radiation source positions, and
wherein the synthesized two-dimensional image, which corresponds to a projection image in a case where the object is irradiated with radiation from the virtual radiation source position, is generated by performing a projection process or an addition process on the plurality of tomographic images in a direction corresponding to the virtual radiation source position.

14. A non-transitory computer-readable storage medium storing a program that causes a computer to perform:
a reconstruction process of reconstructing a plurality of tomographic images from a plurality of projection images obtained by tomosynthesis imaging that irradiates an object with radiation from a radiation source at a plurality of predetermined radiation source positions;
a synthesis process of synthesizing the plurality of tomographic images to generate a synthesized two-dimensional image as a projection image based on a virtual radiation source position;
a projection image selection process of selecting a projection image corresponding to a predetermined radiation source position closest to the virtual radiation source position among the plurality of predetermined radiation source positions;
an anatomical structure extraction process of extracting anatomical structures from the selected projection image; and
a display process of displaying an extraction result of the anatomical structures on a display device together with the synthesized two-dimensional image,
wherein the virtual radiation source position is a position different from the plurality of predetermined radiation source positions or a position that coincides with one of the plurality of predetermined radiation source positions, and
wherein, in the synthesis process, the synthesized two-dimensional image, which corresponds to a projection image in a case where the object is irradiated with radiation from the virtual radiation source position, is generated by performing a projection process or an addition process on the plurality of tomographic images in a direction corresponding to the virtual radiation source position.

* * * * *